US007247308B2

(12) United States Patent
Martin et al.

(10) Patent No.: US 7,247,308 B2
(45) Date of Patent: Jul. 24, 2007

(54) *STREPTOCOCCUS PYOGENES* ANTIGENS

(75) Inventors: Denis Martin, St. Augustin (CA); Josee Hamel, Sillery (CA); Bernard Brodeur, Sillery (CA); Stephane Rioux, Beauport (CA); Martine Boyer, Ste-Foy (CA)

(73) Assignee: ID Biomedical Corporation, Laval, Quebec (CA)

( * ) Notice: Subject to any disclaimer, the term of this patent is extended or adjusted under 35 U.S.C. 154(b) by 0 days.

(21) Appl. No.: 10/332,231

(22) PCT Filed: Jul. 6, 2001

(86) PCT No.: PCT/CA01/01001

§ 371 (c)(1),
(2), (4) Date: Apr. 22, 2003

(87) PCT Pub. No.: WO02/04495

PCT Pub. Date: Jan. 17, 2002

(65) Prior Publication Data

US 2003/0165528 A1 Sep. 4, 2003

Related U.S. Application Data

(60) Provisional application No. 60/216,465, filed on Jul. 6, 2000.

(51) Int. Cl.
*A61K 39/09* (2006.01)

(52) U.S. Cl. .............................. 424/244.1; 424/234.1; 424/185.1; 424/190.1; 530/300; 530/350

(58) Field of Classification Search ............ 424/244.1, 424/234.1, 185.1, 190.1; 530/300, 350
See application file for complete search history.

(56) References Cited

FOREIGN PATENT DOCUMENTS

EP 0 916 726 A 5/1999

OTHER PUBLICATIONS

Kil et al. Submitted May 1994. Gencore Accession No. Q54524 (corresponding to Infect. Immun. 62(2): 2440-2449).*
Kil et al. Infect. Immun. 1994. 62(6): 2440-2449.*
Mikayama et al. (Nov. 1993. Proc.Natl.Acad.Sci. USA, vol. 90: 10056-10060).*
Rudinger et al. (Jun. 1976. Peptide Hormones. Biol. Council. pp. 5-7).*
Database Swall 'Online! EBI; Nov. 1, 1996, "KDa protein (ORFI) and 67 KDa myosin-crossreactive streptococcal antigen", XP002194338, Acc. No. Q54524.
Database EMBL/GENBANK/DDBJ 'Online! EBI; Aug. 5, 1994, "42 KDa protein (ORFI) and 67 KDa myosin-crossreactive streptococcal antigen gene, complete cds", XP002194339, Acc. No. SP09352.
Database Swall 'Online! EBI; Jun. 1, 2001, "Putative 42 KDa protein of S. pyogenes (encoded by gene spy0469)", XP002194340, Acc. No. Q9A147.

* cited by examiner

*Primary Examiner*—Jennifer E. Graser
(74) *Attorney, Agent, or Firm*—Seed IP Law Group PLLC

(57) ABSTRACT

The present invention relates to antigens, more particularly an antigen of *Streptococcus pygenes* (also called group A *Streptococcus* (GAS)) bacterial pathogen which is useful as vaccine component for therapy and/or prophylaxis.

11 Claims, 15 Drawing Sheets

Figure 1

```
   1 ATGATTATTA CTAAAAAGAG CTTATTTGTG ACAAGTGTCG CTTTGTCGTT AGCACCTTTG
  61 GCGACAGCAC AGGCACAAGA GTGGACACCA CGATCGGTTA CAGAAATCAA GTCTGAACTC
 121 GTCCTAGTTG ATAATGTTTT TACTTATACT GTAAAATACG GTGACACTTT AAGCACAATT
 181 GCTGAAGCAA TGGGAATTGA TGTGCATGTC TTAGGAGATA TTAATCATAT TGCTAATATT
 241 GACTTAATTT TTCCAGACAC GATCCTAACA GCCAACTACA ACCAACACGG TCAGGCAACG
 301 ACTTTGACGG TTCAAGCGCC TGCTTCTAGT CCAGCTAGCG TTAGTCATGT ACCTAGCAGT
 361 GAGCCATTAC CCCAAGCATC TGCCACCTCT CAATCGACTG TTCCTATGGC ACCATCTGCG
 421 ACACCATCTG ATGTCCCAAC GACACCATTC GCATCTGCAA AGCCAGATAG TTCTGTGACA
 481 GCGTCATCTG AGCTCACATC GTCAACGAAT GATGTTTCGA CTGAGTTGTC TAGCGAATCA
 541 CAAAAGCAGC CAGAAGTACC ACAAGAAGCA GTTCCAACTC CTAAAGCAGC TGAAACGACT
 601 GAAGTCGAAC CTAAGACAGA CATCTCAGAG GATTCAACTT CAGCTAATAG GCCTGTACCT
 661 AACGAGAGTG CTTCAGAAGA AGTTTCTTCT GCGGCCCCAG CACAAGCCCC AGCAGAAAAA
 721 GAAGAAACCT CTGCGCCAGC AGCACAAAAA GCTGTAGCTG ACACCACAAG TGTTGCAACC
 781 TCAAATGGCC TTTCTTACGC TCCAAACCAT GCCTACAATC CAATGAATGC AGGGCTTCAA
 841 CCACAAACAG CAGCCTTCAA AGAAGAAGTG GCTTCTGCCT TTGGTATTAC GTCATTTAGT
 901 GGTTACCGTC CAGGTGATCC AGGAGATCAT GGTAAAGGTT TGGCCATTGA TTTTATGGTG
 961 CCTGAAAATT CTGCTCTTGG TGATCAAGTT GCTCAATATG CCATTGACCA TATGGCAGAG
1021 CGTGGTATTT CATACGTTAT TTGGAAACAG CGATTCTATG CGCCATTTGC AAGTATTTAC
1081 GGACCAGCCT ACACATGGAA CCCCATGCCA GATCGCGGCA GTATTACAGA AAACCATTAT
1141 GATCATGTTC ATGTCTCCTT TAATGCTTAA (SEQ ID NO:1)
```

Figure 2

```
  1 MIITKKSLFV TSVALSLAPL ATAQAQEWTP RSVTEIKSEL VLVDNVFTYT VKYGDTLSTI
 61 AEAMGIDVHV LGDINHIANI DLIFPDTILT ANYNQHGQAT TLTVQAPASS PASVSHVPSS
121 EPLPQASATS QSTVPMAPSA TPSDVPTTPF ASAKPDSSVT ASSELTSSTN DVSTELSSES
181 QKQPEVPQEA VPTPKAAETT EVEPKTDISE DSTSANRPVP NESASEEVSS AAPAQAPAEK
241 EETSAPAAQK AVADTTSVAT SNGLSYAPNH AYNPMNAGLQ PQTAAFKEEV ASAFGITSFS
301 GYRPGDPGDH GKGLAIDFMV PENSALGDQV AQYAIDHMAE RGISYVIWKQ RFYAPFASIY
361 GPAYTWNPMP DRGSITENHY DHVHVSFNA* (SEQ ID NO:2)
```

Figure 3

1 ATGATTATTA CTAAAAAGAG CTTATTTGTG ACAAGTGTCG CTTTGTCGTT AGCACCTTTG
61 GCGACAGCGC AGGCACAAGA GTGGACACCA CGATCGGTTA CAGAAATCAA GTCTGAACTC
121 GTCCTAGTTG ATAATGTTTT TACTTATATA GTAAAATACG GTGACACTTT AAGCACAATT
181 GCTGAAGCAA TGGGGATTGA TGTGCATGTC TTAGGAGATA TTAATCATAT TGCTAATATT
241 GACTTAATTT TTCCAGACAC GATCCTAACA GCAAACTACA ACCAACACGG TCAGGCAACG
301 ACTTTGACGG TTCAAGCACC TGCTTCTAGT CCATCTAGCG TTAGTCATGT ACCTAGCAGT
361 GAGCCATTAC CCCAAGCATC TGCCACCTCT CAACCGACTG TTCCTATGGC ACCATCTGCG
421 ACACCATCTG ATGTCCCAAC GACACCATTC GCATCTGCAA AGCCAGATAG TTCTGTGACA
481 GCGTCATCTG AGCTCACATC GTCAACGAAT GATGTTTCGA CTGAGTTGTC TAGCGAATCA
541 CAAAAGCAGC CAGAAGTACC ACAAGAAGCA GTTCCAACTC CTAAAGCAGC TGAACCGACT
601 GAAGTCGAAC CTAAGACAGA CATCTCAGAA GACCCAACTT CAGCTAATAG GCCTGTACCT
661 AACGAGAGTG CTTCAGAAGA AGCTTCTTCT GCGGCCCCAG CACAAGCTCC AGCAGAAAAA
721 GAAGAAACCT CTCAGATGTT AACTGCGCCA GCAGCACAAA AAGCTGTAGC TGACACCACA
781 AGTGTTGCAA CCTCAAACGG CCTTTCTTAC GCTCCAAACC ATGCCTACAA TCCAATGAAT
841 GCAGGGCTTC AACCACAAAC AGCAGCCTTC AAAGAAGAAG TGGCTTCTGC CTTTGGTATT
901 ACGTCATTTA GTGGTTACCG TCCAGGAGAT CCAGGAGATC ATGGTAAAGG ATTAGCCATT
961 GACTTTATGG TACCGGTTAG CTCTACGCTT GGTGATCAAG TTGCTCAATA TGCCATTGAC
1021 CATATGGCAG AGCGTGGTAT TTCATACGTT ATTTGGAAAC AGCGATTCTA TGCGCCATTT
1081 GCAAGTATTT ACGGACCAGC CTACACATGG AACCCCATGC CAGATCGCGG CAGTATTACA
1141 GAAAACCATT ATGATCATGT TCATGTCTCC TTTAATGCTT AA (SEQ ID NO:3)

Figure 4

1 MIITKKSLFV TSVALSLAPL ATAQAQEWTP RSVTEIKSEL VLVDNVFTYI VKYGDTLSTI
61 AEAMGIDVHV LGDINHIANI DLIFPDTILT ANYNQHGQAT TLTVQAPASS PSSVSHVPSS
121 EPLPQASATS QPTVPMAPSA TPSDVPTTPF ASAKPDSSVT ASSELTSSTN DVSTELSSES
181 QKQPEVPQEA VPTPKAAEPT EVEPKTDISE DPTSANRPVP NESASEEASS AAPAQAPAEK
241 EETSQMLTAP AAQKAVADTT SVATSNGLSY APNHAYNPMN AGLQPQTAAF KEEVASAFGI
301 TSFSGYRPGD PGDHGKGLAI DFMVPVSSTL GDQVAQYAID HMAERGISYV IWKQRFYAPF
361 ASIYGPAYTW NPMPDRGSIT ENHYDHVHVS FNA* (SEQ ID NO:4)

Figure 5

```
1    ATGATTATTA CTAAAAAGAG CTTATTTGTG ACAAGTGTCG CTTTGTCGTT AGTACCTTTG
61   GCGACAGCGC AGGCACAAGA GTGGACACCA CGATCGGTTA CAGAAATCAA GTCTGAACTC
121  GTCCTAGTTG ATAATGTTTT TACTTATACT GTAAAATACG GTGACACTTT AAGCACAATT
181  GCTGAAGCAA TGGGGATTGA TGTGCATGTC TTAGGAGATA TTAATCATAT TGCTAATATT
241  GACCTAATTT TTCCAGACAC GATCCTAACA GCAAACTACA ATCAACACGG TCAGGCAACG
301  AATTTGACGG TTCAAGCACC TGCTTCTAGT CCAGCTAGCG TTAGTCATGT ACCTAGCAGT
361  GAGCCATTAC CCCAAGCATC TGCCACCTCT CAACCGACTG TTCCTATGGC ACCACCTGCG
421  ACACCATCTG ATGTCCCAAC GACACCATTC GCATCTGCAA AGCCAGATAG TTCTGTGACA
481  GCGTCATCTG AGCTCACATC GTCAACGAAT GATGTTTCGA CTGAGTTGTC TAGCGAATCA
541  CAAAAGCAGC CAGAAGTACC ACAAGAAGCA GTTCCAACTC CTAAAGCAGC TGAAACGACT
601  GAAGTCGAAC CTAAGACAGA CATCTCAGAA GCCCCAACTT CAGCTAATAG GCCTGTACCT
661  AACGAGAGTG CTTCAGAAGA AGTTTCTTCT GCGGCCCCAG CACAAGCCCC AGCAGAAAAA
721  GAAGAAACCT CTGCGCCAGC AGCACAAAAA GCTGTAGCTG ACACCACAAG TGTTGCAACC
781  TCAAATGGCC TTTCTTACGC TCCAAACCAT GCCTACAATC CAATGAATGC AGGGCTTCAA
841  CCACAAACAG CAGCCTTCAA AGAAGAAGTG GCTTCTGCCT TTGGTATTAC GTCATTTAGT
901  GGTTACCGTC CAGGTGATCC AGGAGATCAT GGTAAAGGTT TGGCCATTGA TTTTATGGTG
961  CCTGAAAATT CTGCTCTTGG TGATCAAGTT GCTCAATATG CCATTGACCA TATGGCAGAG
1021 CGTGGTATTT CATACGTTAT TTGGAAACAG CGATTCTATG CGCCATTTGC AAGTATTTAC
1081 GGACCAGCCT ACACATGGAA CCCCATGCCA GATCGCGGCA GTATTACAGA AAACCATTAT
1141 GATCATGTTC ATGTCTCCTT TAATGCTTAA (SEQ ID NO:5)
```

Figure 6

```
1    MIITKKSLFV TSVALSLVPL ATAQAQEWTP RSVTEIKSEL VLVDNVFTYT VKYGDTLSTI
61   AEAMGIDVHV LGDINHIANI DLIFPDTILT ANYNQHGQAT NLTVQAPASS PASVSHVPSS
121  EPLPQASATS QPTVPMAPPA TPSDVPTTPF ASAKPDSSVT ASSELTSSTN DVSTELSSES
181  QKQPEVPQEA VPTPKAAETT EVEPKTDISE APTSANRPVP NESASEEVSS AAPAQAPAEK
241  EETSAPAAQK AVADTTSVAT SNGLSYAPNH AYNPMNAGLQ PQTAAFKEEV ASAFGITSFS
301  GYRPGDPGDH GKGLAIDFMV PENSALGDQV AQYAIDHMAE RGISYVIWKQ RFYAPFASIY
361  GPAYTWNPMP DRGSITENHY DHVHVSFNA* (SEQ ID NO:6)
```

Figure 7

1 ATGATTATTA CTAAAAAGAG CTTATTTGTG ACAAGTGTCG CTTTGTCGTT AGCACCTTTG

61 GCGACAGCGC AGGCACAAGA GTGGACACCA CGATCGGTTA CAGAAATCAA GTCTGAACTC

121 GTCCTAGTTG ATAATGTTTT TACTTATACA GTAAAATACG GTGACACTTT AAGCACAATT

181 GCTGAAGCAA TGGGGATTGA TGTGCATGTC TTAGGAGATA TTAATCATAT TGCTAATATT

241 GACTTAATTT TTCCAGACAC GATCCTAACA GCAAACTACA ATCAACACGG TCAGGCAACG

301 ACTTTGACGG TTCAAGCACC TGCTTCTAGT CCAGCTAGCG TTAGTCATGT ACCTAGCAGT

361 GAGCCATTAC CCCAAGCATC TGCCACCTCT CAACCGACTG TTCCTATGGC ACCATCTGCG

421 ACACCATTAG CATCTGCAAA GCCAGATAGT TCTGTGACAG CGTCATCTGA GCTCACATCG

481 TCAACGAATG ATGTTTCGAC TGAGTCGTCT AGCGAATCAC AAAAGCAGCC AGAAGTACCA

541 CAAGAAGCAG TTCCAACTCC TAAAGCAGCT GAAACGACTG AAGTCGAACC TAAGACAGAC

601 ATCTCAGAAG ACCCAACTTC AGCTAATAGG CCTGTACCTA ACGAGAGTGC TTCAGAAGAA

661 GTTTCTTCTG CGGCCCCAGC ACAAGCCCCA GCAGAAAAAG AAGAAACCTC TGCGCCAGCA

721 GCACAAAAAG CTGTAGCTGA CACCACAAGT GTTGCAACCT CAAACGGCCT TTCTTACGCT

781 CCAAACCATG CCTACAATCC AATGAATGCA GGGCTTCAAC CACAAACAGC AGCCTTCAAA

841 GAAGAAGTGG CTTCTGCCTT TGGTATTACG TCATTTAGTG GTTACCGTCC AGGTGACCCA

901 GGAGATCATG GTAAAGGTTT GGCCATTGAT TTTATGGTGC CTGAAAATTC TGCTCTTGGT

961 GATCAAGTTG CTCAATATGC CATTGACCAT ATGGCAGAGC GTGGTATTTC ATACGTTATT

1021 TGGAAACAGC GATTCTATGC GCCATTTGCA AGTATTTACG GACCAGCTTA CACATGGAAC

1081 CCCATGCCAG ATCGCGGCAG TATTACAGAA AACCATTATG ATCATGTTCA TGTCTCCTTT

1141 AATGCTTAA (SEQ ID NO:7)

Figure 8

1 MIITKKSLFV TSVALSLAPL ATAQAQEWTP RSVTEIKSEL VLVDNVFTYT VKYGDTLSTI

61 AEAMGIDVHV LGDINHIANI DLIFPDTILT ANYNQHGQAT TLTVQAPASS PASVSHVPSS

121 EPLPQASATS QPTVPMAPSA TPLASAKPDS SVTASSELTS STNDVSTESS SESQKQPEVP

181 QEAVPTPKAA ETTEVEPKTD ISEDPTSANR PVPNESASEE VSSAAPAQAP AEKEETSAPA

241 AQKAVADTTS VATSNGLSYA PNHAYNPMNA GLQPQTAAFK EEVASAFGIT SFSGYRPGDP

301 GDHGKGLAID FMVPENSALG DQVAQYAIDH MAERGISYVI WKQRFYAPFA SIYGPAYTWN

361 PMPDRGSITE NHYDHVHVSF NA* (SEQ ID NO:8)

Figure 9

```
1    CAAGAGTGGA CACCACGATC GGTTACAGAA ATCAAGTCTG AACTCGTCCT AGTTGATAAT
61   GTTTTTACTT ATACTGTAAA ATACGGTGAC ACTTTAAGCA CAATTGCTGA AGCAATGGGA
121  ATTGATGTGC ATGTCTTAGG AGATATTAAT CATATTGCTA ATATTGACTT AATTTTTCCA
181  GACACGATCC TAACAGCCAA CTACAACCAA CACGGTCAGG CAACGACTTT GACGGTTCAA
241  GCGCCTGCTT CTAGTCCAGC TAGCGTTAGT CATGTACCTA GCAGTCAGCC ATTACCCCAA
301  GCATCTGCCA CCTCTCAATC GACTGTTCCT ATGGCACCAT CTGCGACACC ATCTGATGTC
361  CCAACGACAC CATTCGCATC TGCAAAGCCA GATAGTTCTG TGACAGCGTC ATCTGAGCTC
421  ACATCGTCAA CGAATGATGT TTCGACTGAG TTGTCTAGCG AATCACAAAA GCAGCCAGAA
481  GTACCACAAG AAGCAGTTCC AACTCCTAAA GCAGCTGAAA CGACTGAAGT CGAACCTAAG
541  ACAGACATCT CAGAGGATTC AACTTCAGCT AATAGGCCTG TACCTAACGA GAGTGCTTCA
601  GAAGAAGTTT CTTCTGCGGC CCCAGCACAA GCCCCAGCAG AAAAAGAAGA AACCTCTGCG
661  CCAGCAGCAC AAAAAGCTGT AGCTGACACC ACAAGTGTTG CAACCTCAAA TGGCCTTTCT
721  TACGCTCCAA ACCATGCCTA CAATCCAATG AATGCAGGGC TTCAACCACA AACAGCAGCC
781  TTCAAAGAAG AAGTGGCTTC TGCCTTTGGT ATTACGTCAT TTAGTGGTTA CCGTCCAGGT
841  GATCCAGGAG ATCATGGTAA AGGTTTGGCC ATTGATTTTA TGGTGCCTGA AAATTCTGCT
901  CTTGGTGATC AAGTTGCTCA ATATGCCATT GACCATATGG CAGAGCGTGG TATTTCATAC
961  GTTATTTGGA AACAGCGATT CTATGCGCCA TTTGCAAGTA TTTACGGACC AGCCTACACA
1021 TGGAACCCCA TGCCAGATCG CGGCAGTATT ACAGAAAACC ATTATGATCA TGTTCATGTC
1081 TCCTTTAATG CTTAA (SEQ ID NO:9)
```

Figure 10

```
1    QEWTPRSVTE IKSELVLVDN VFTYTVKYGD TLSTIAEAMG IDVHVLGDIN HIANIDLIFP
61   DTILTANYNQ HGQATTLTVQ APASSPASVS HVPSSEPLPQ ASATSQSTVP MAPSATPSDV
121  PTTPFASAKP DSSVTASSEL TSSTNDVSTE LSSESQKQPE VPQEAVPTPK AAETTEVEPK
181  TDISEDSTSA NRPVPNESAS EEVSSAAPAQ APAEKEETSA PAAQKAVADT TSVATSNGLS
241  YAPNHAYNPM NAGLQPQTAA FKEEVASAFG ITSFSGYRPG DPGDHGKGLA IDFMVPENSA
301  LGDQVAQYAI DHMAERGISY VIWKQRFYAP FASIYGPAYT WNPMPDRGSI TENHYDHVHV
361  SFNA* (SEQ ID NO:10)
```

Figure 11

1 CAAGAGTGGA CACCACGATC GGTTACAGAA ATCAAGTCTG AACTCGTCCT AGTTGATAAT
61 GTTTTTACTT ATATAGTAAA ATACGGTGAC ACTTTAAGCA CAATTGCTGA AGCAATGGGG
121 ATTGATGTGC ATGTCTTAGG AGATATTAAT CATATTGCTA ATATTGACTT AATTTTTCCA
181 GACACGATCC TAACAGCAAA CTACAACCAA CACGGTCAGG CAACGACTTT GACGGTTCAA
241 GCACCTGCTT CTAGTCCATC TAGCGTTAGT CATGTACCTA GCAGTGAGCC ATTACCCCAA
301 GCATCTGCCA CCTCTCAACC GACTGTTCCT ATGGCACCAT CTGCGACACC ATCTGATGTC
361 CCAACGACAC CATTCGCATC TGCAAAGCCA GATAGTTCTG TGACAGCGTC ATCTGAGCTC
421 ACATCGTCAA CGAATGATGT TTCGACTGAG TTGTCTAGCG AATCACAAAA GCAGCCAGAA
481 GTACCACAAG AAGCAGTTCC AACTCCTAAA GCAGCTGAAC CGACTGAAGT CGAACCTAAG
541 ACAGACATCT CAGAAGACCC AACTTCAGCT AATAGGCCTG ACCTAACGA GAGTGCTTCA
601 GAAGAAGCTT CTTCTGCGGC CCCAGCACAA GCTCCAGCAG AAAAAGAAGA AACCTCTCAG
661 ATGTTAACTG CGCCAGCAGC ACAAAAAGCT GTAGCTGACA CCACAAGTGT TGCAACCTCA
721 AACGGCCTTT CTTACGCTCC AAACCATGCC TACAATCCAA TGAATGCAGG GCTTCAACCA
781 CAAACAGCAG CCTTCAAAGA AGAAGTGGCT TCTGCCTTTG GTATTACGTC ATTTAGTGGT
841 TACCGTCCAG GAGATCCAGG AGATCATGGT AAAGGATTAG CCATTGACTT TATGGTACCG
901 GTTAGCTCTA CGCTTGGTGA TCAAGTTGCT CAATATGCCA TTGACCATAT GGCAGAGCGT
961 GGTATTTCAT ACGTTATTTG GAAACAGCGA TTCTATGCGC CATTTGCAAG TATTTACGGA
1021 CCAGCCTACA CATGGAACCC CATGCCAGAT CGCGGCAGTA TTACAGAAAA CCATTATGAT
1081 CATGTTCATG TCTCCTTTAA TGCTTAA (SEQ ID NO:11)

Figure 12

1 QEWTPRSVTE IKSELVLVDN VFTYIVKYGD TLSTIAEAMG IDVHVLGDIN HIANIDLIFP
61 DTILTANYNQ HGQATTLTVQ APASSPSSVS HVPSSEPLPQ ASATSQPTVP MAPSATPSDV
121 PTTPFASAKP DSSVTASSEL TSSTNDVSTE LSSESQKQPE VPQEAVPTPK AAEPTEVEPK
181 TDISEDPTSA NRPVPNESAS EEASSAAPAQ APAEKEETSQ MLTAPAAQKA VADTTSVATS
241 NGLSYAPNHA YNPMNAGLQP QTAAFKEEVA SAFGITSFSG YRPGDPGDHG KGLAIDFMVP
301 VSSTLGDQVA QYAIDHMAER GISYVIWKQR FYAPFASIYG PAYTWNPMPD RGSITENHYD
361 HVHVSFNA* (SEQ ID NO:12)

Figure 13

1 CAAGAGTGGA CACCACGATC GGTTACAGAA ATCAAGTCTG AACTCGTCCT AGTTGATAAT
61 GTTTTTACTT ATACTGTAAA ATACGGTGAC ACTTTAAGCA CAATTGCTGA AGCAATGGGG
121 ATTGATGTGC ATGTCTTAGG AGATATTAAT CATATTGCTA ATATTGACCT AATTTTTCCA
181 GACACGATCC TAACAGCAAA CTACAATCAA CACGGTCAGG CAACGAATTT GACGGTTCAA
241 GCACCTGCTT CTAGTCCAGC TAGCGTTAGT CATGTACCTA GCAGTGAGCC ATTACCCCAA
301 GCATCTGCCA CCTCTCAACC GACTGTTCCT ATGGCACCAC CTGCGACACC ATCTGATGTC
361 CCAACGACAC CATTCGCATC TGCAAAGCCA GATAGTTCTG TGACAGCGTC ATCTGAGCTC
421 ACATCGTCAA CGAATGATGT TTCGACTGAG TTGTCTAGCG AATCACAAAA GCAGCCAGAA
481 GTACCACAAG AAGCAGTTCC AACTCCTAAA GCAGCTGAAA CGACTGAAGT CGAACCTAAG
541 ACAGACATCT CAGAAGCCCC AACTTCAGCT AATAGGCCTG TACCTAACGA GAGTGCTTCA
601 GAAGAAGTTT CTTCTGCGGC CCCAGCACAA GCCCCAGCAG AAAAAGAAGA AACCTCTGCG
661 CCAGCAGCAC AAAAAGCTGT AGCTGACACC ACAAGTGTTG CAACCTCAAA TGGCCTTTCT
721 TACGCTCCAA ACCATGCCTA CAATCCAATG AATGCAGGGC TTCAACCACA AACAGCAGCC
781 TTCAAAGAAG AAGTGGCTTC TGCCTTTGGT ATTACGTCAT TTAGTGGTTA CCGTCCAGGT
841 GATCCAGGAG ATCATGGTAA AGGTTTGGCC ATTGATTTTA TGGTGCCTGA AAATTCTGCT
901 CTTGGTGATC AAGTTGCTCA ATATGCCATT GACCATATGG CAGAGCGTGG TATTTCATAC
961 GTTATTTGGA AACAGCGATT CTATGCGCCA TTTGCAAGTA TTTACGGACC AGCCTACACA
1021 TGGAACCCCA TGCCAGATCG CGGCAGTATT ACAGAAAACC ATTATGATCA TGTTCATGTC
1081 TCCTTTAATG CTTAA (SEQ ID NO:13)

Figure 14

1 QEWTPRSVTE IKSELVLVDN VFTYTVKYGD TLSTIAEAMG IDVHVLGDIN HIANIDLIFP
61 DTILTANYNQ HGQATNLTVQ APASSPASVS HVPSSEPLPQ ASATSQPTVP MAPPATPSDV
121 PTTPFASAKP DSSVTASSEL TSSTNDVSTE LSSESQKQPE VPQEAVPTPK AAETTEVEPK
181 TDISEAPTSA NRPVPNESAS EEVSSAAPAQ APAEKEETSA PAAQKAVADT TSVATSNGLS
241 YAPNHAYNPM NAGLQPQTAA FKEEVASAFG ITSFSGYRPG DPGDHGKGLA IDFMVPENSA
301 LGDQVAQYAI DHMAERGISY VIWKQRFYAP FASIYGPAYT WNPMPDRGSI TENHYDHVHV
361 SFNA* (SEQ ID NO:14)

Figure 15

1 CAAGAGTGGA CACCACGATC GGTTACAGAA ATCAAGTCTG AACTCGTCCT AGTTGATAAT
61 GTTTTTACTT ATACAGTAAA ATACGGTGAC ACTTTAAGCA CAATTGCTGA AGCAATGGGG
121 ATTGATGTGC ATGTCTTAGG AGATATTAAT CATATTGCTA ATATTGACTT AATTTTTCCA
181 GACACGATCC TAACAGCAAA CTACAATCAA CACGGTCAGG CAACGACTTT GACGGTTCAA
241 GCACCTGCTT CTAGTCCAGC TAGCGTTAGT CATGTACCTA GCAGTGAGCC ATTACCCCAA
301 GCATCTGCCA CCTCTCAACC GACTGTTCCT ATGGCACCAT CTGCGACACC ATTAGCATCT
361 GCAAAGCCAG ATAGTTCTGT GACAGCGTCA TCTGAGCTCA CATCGTCAAC GAATGATGTT
421 TCGACTGAGT CGTCTAGCGA ATCACAAAAG CAGCCAGAAG TACCACAAGA AGCAGTTCCA
481 ACTCCTAAAG CAGCTGAAAC GACTGAAGTC GAACCTAAGA CAGACATCTC AGAAGACCCA
541 ACTTCAGCTA ATAGGCCTGT ACCTAACGAG AGTGCTTCAG AAGAAGTTTC TTCTGCGGCC
601 CCAGCACAAG CCCCAGCAGA AAAAGAAGAA ACCTCTGCGC CAGCAGCACA AAAAGCTGTA
661 GCTGACACCA CAAGTGTTGC AACCTCAAAC GGCCTTTCTT ACGCTCCAAA CCATGCCTAC
721 AATCCAATGA ATGCAGGGCT TCAACCACAA ACAGCAGCCT TCAAAGAAGA AGTGGCTTCT
781 GCCTTTGGTA TTACGTCATT TAGTGGTTAC CGTCCAGGTG ACCCAGGAGA TCATGGTAAA
841 GGTTTGGCCA TTGATTTTAT GGTGCCTGAA AATTCTGCTC TTGGTGATCA AGTTGCTCAA
901 TATGCCATTG ACCATATGGC AGAGCGTGGT ATTTCATACG TTATTTGGAA ACAGCGATTC
961 TATGCGCCAT TTGCAAGTAT TTACGGACCA GCTTACACAT GGAACCCCAT GCCAGATCGC
1021 GGCAGTATTA CAGAAAACCA TTATGATCAT GTTCATGTCT CCTTTAATGC TTAA (SEQ ID NO:15)

Figure 16

1 QEWTPRSVTE IKSELVLVDN VFTYTVKYGD TLSTIAEAMG IDVHVLGDIN HIANIDLIFP
61 DTILTANYNQ HGQATTLTVQ APASSPASVS HVPSSEPLPQ ASATSQPTVP MAPSATPLAS
121 AKPDSSVTAS SELTSSTNDV STESSSESQK QPEVPQEAVP TPKAAETTEV EPKTDISEDP
181 TSANRPVPNE SASEEVSSAA PAQAPAEKEE TSAPAAQKAV ADTTSVATSN GLSYAPNHAY
241 NPMNAGLQPQ TAAFKEEVAS AFGITSFSGY RPGDPGDHGK GLAIDFMVPE NSALGDQVAQ
301 YAIDHMAERG ISYVIWKQRF YAPFASIYGP AYTWNPMPDR GSITENHYDH VHVSFNA*
(SEQ ID NO:16)

Figure 17

```
12384       1 ATGATTATTACTAAAAAGAGCTTATTTGTGACAAGTGTCGCTTTGTCGTT   50
2699        1 ATGATTATTACTAAAAAGAGCTTATTTGTGACAAGTGTCGCTTTGTCGTT   50
B514        1 ATGATTATTACTAAAAAGAGCTTATTTGTGACAAGTGTCGCTTTGTCGTT   50
Spy57       1 ATGATTATTACTAAAAAGAGCTTATTTGTGACAAGTGTCGCTTTGTCGTT   50
U09352      1 ATGATTATTACTAAAAAGAGTTTATTTGTGACAAGTGTCGCTTTGTCGTT   50
Oklahoma    1 ATGATTATTACTAAAAAGAGCTTATTTGTGACAAGTGTCGCTTTGTCGTT   50
              ******************** *****************************

12384      51 AGCACCTTTGGCGACAGCACAGGCACAAGAGTGGACACCACGATCGGTTA  100
2699       51 AGCACCTTTGGCGACAGCGCAGGCACAAGAGTGGACACCACGATCGGTTA  100
B514       51 AGCACCTTTGGCGACAGCGCAGGCACAAGAGTGGACACCACGATCGGTTA  100
Spy57      51 AGTACCTTTGGCGACAGCGCAGGCACAAGAGTGGACACCACGATCGGTTA  100
U09352     51 AGCACCTTTGGCGACAGCGCAGGCACAAGAGTGGACACCACGATCGGTTA  100
Oklahoma   51 AGTACCTTTGGCGACAGCGCAGGCACAAGAGTGGACACCACGATCGGTTA  100
              ** *************** *******************************

12384     101 CAGAAATCAAGTCTGAACTCGTCCTAGTTGATAATGTTTTTACTTATACT  150
2699      101 CAGAAATCAAGTCTGAACTCGTCCTAGTTGATAATGTTTTTACTTATATA  150
B514      101 CAGAAATCAAGTCTGAACTCGTCCTAGTTGATAATGTTTTTACTTATACA  150
Spy57     101 CAGAAATCAAGTCTGAACTCGTCCTAGTTGATAATGTTTTTACTTATACT  150
U09352    101 CACAAATCAAGTCTGAACTCGTCCTAGTTGATAATGTTTTTACTTATACA  150
Oklahoma  101 CAGAAATCAAGTCTGAACTCGTCCTAGTTGATAATGTTTTTACTTATACT  150
              ** ***********************************************

12384     151 GTAAAATACGGTGACACTTTAAGCACAATTGCTGAAGCAATGGGAATTGA  200
2699      151 GTAAAATACGGTGACACTTTAAGCACAATTGCTGAAGCAATGGGGATTGA  200
B514      151 GTAAAATACGGTGACACTTTAAGCACAATTGCTGAAGCAATGGGGATTGA  200
Spy57     151 GTAAAATACGGTGACACTTTAAGCACAATTGCTGAAGCAATGGGGATTGA  200
U09352    151 GTAAAATACGGTGACACTTTAAGCACAATTGCTGAAGCAATGGGGATTGA  200
Oklahoma  151 GTAAAATACGGTGACACTTTAAGCACAATTGCTGAAGCAATGGGGATTGA  200
              ******************************************** *****

12384     201 TGTGCATGTCTTAGGAGATATTAATCATATTGCTAATATTGACTTAATTT  250
2699      201 TGTGCATGTCTTAGGAGATATTAATCATATTGCTAATATTGACTTAATTT  250
B514      201 TGTGCATGTCTTAGGAGATATTAATCATATTGCTAATATTGACTTAATTT  250
Spy57     201 TGTGCATGTCTTAGGAGATATTAATCATATTGCTAATATTGACCTAATTT  250
U09352    201 TGTGCATGTCTTAGGAGATATTAATCATATTGCTAATATTGACTTAATTT  250
Oklahoma  201 TGTGCATGTCTTAGGAGATATTAATCATATTGCTAATATTGACCTAATTT  250
              ******************************************* ******

12384     251 TTCCAGACACGATCCTAACAGCCAACTACAACCAACACGGTCAGGCAACG  300
2699      251 TTCCAGACACGATCCTAACAGCAAACTACAACCAACACGGTCAGGCAACG  300
B514      251 TTCCAGACACGATCCTAACAGCAAACTACAATCAACACGGTCAGGCAACG  300
Spy57     251 TTCCAGACACGATCCTAACAGCAAACTACAATCAACACGGTCAGGCAACG  300
U09352    251 TTCCAGACACGATCCTAACAGCAAACTACAACCAACACGGTCAGGCAACG  300
Oklahoma  251 TTCCAGACACGATCCTAACAGCAAACTACAATCAACACGGTCAGGCAACG  300
              ********************** ******** ******************

12384     301 ACTTTGACGGTTCAAGCGCCTGCTTCTAGTCCAGCTAGCGTTAGTCATGT  350
2699      301 ACTTTGACGGTTCAAGCACCTGCTTCTAGTCCATCTAGCGTTAGTCATGT  350
B514      301 ACTTTGACGGTTCAAGCACCTGCTTCTAGTCCAGCTAGCGTTAGTCATGT  350
Spy57     301 AATTTGACGGTTCAAGCACCTGCTTCTAGTCCAGCTAGCGTTAGTCATGT  350
U09352    301 ACTTTGACGGTTCAAGCGCCTGCTTCTAGTCCAGCTAGCGTTAGTCATGT  350
Oklahoma  301 AATTTGACGGTTCAAGCACCTGCTTCTAGTCCAGCTAGCGTTAGTCATGT  350
              * *************** *************** ****************
```

```
12384     351 ACCTAGCAGTGAGCCATTACCCCAAGCATCTGCCACCTCTCAATCGACTG  400
2699      351 ACCTAGCAGTGAGCCATTACCCCAAGCATCTGCCACCTCTCAACCGACTG  400
B514      351 ACCTAGCAGTGAGCCATTACCCCAAGCATCTGCCACCTCTCAACCGACTG  400
Spy57     351 ACCTAGCAGTGAGCCATTACCCCAAGCATCTGCCACCTCTCAACCGACTG  400
U09352    351 ACCTAGCAGTGAGCCATTACCCCAAGCATCTGCCACCTCTCAATCGACTA  400
Oklahoma  351 ACCTAGCAGTGAGCCATTACCCCAAGCATCTGCCACCTCTCAACCGACTG  400
              *******************************************  *****

12384     401 TTCCTATGGCACCATCTGCGACACCATCTGATGTCCCAACGACACCATTC  450
2699      401 TTCCTATGGCACCATCTGCGACACCATCTGATGTCCCAACGACACCATTC  450
B514      401 TTCCTATGGCACCATCTGCGACACCAT---------------------TA  429
Spy57     401 TTCCTATGGCACCACCTGCGACACCATCTGATGTCCCAACGACACCATTC  450
U09352    401 TTCCTATGGCACCATCTGCGACACCATCTGATGTCCCAACGACACCATTA  450
Oklahoma  401 TTCCTATGGCACCACCTGCGACACCATCTGATGTCCCAACGACACCATTC  450
              ************** ************                     *

12384     451 GCATCTGCAAAGCCAGATAGTTCTGTGACAGCGTCATCTGAGCTCACATC  500
2699      451 GCATCTGCAAAGCCAGATAGTTCTGTGACAGCGTCATCTGAGCTCACATC  500
B514      430 GCATCTGCAAAGCCAGATAGTTCTGTGACAGCGTCATCTGAGCTCACATC  479
Spy57     451 GCATCTGCAAAGCCAGATAGTTCTGTGACAGCGTCATCTGAGCTCACATC  500
U09352    451 GCATCTGCAAAGCCAGATAGTTTTGTGACAGCGTCATCTGAGCTCACATC  500
Oklahoma  451 GCATCTGCAAAGCCAGATAGTTCTGTGACAGCGTCATCTGAGCTCACATC  500
              ********************** ***************************

12384     501 GTCAACGAATGATGTTTCGACTGAGTTGTCTAGCGAATCACAAAAGCAGC  550
2699      501 GTCAACGAATGATGTTTCGACTGAGTTGTCTAGCGAATCACAAAAGCAGC  550
B514      480 GTCAACGAATGATGTTTCGACTGAGTCGTCTAGCGAATCACAAAAGCAGC  529
Spy57     501 GTCAACGAATGATGTTTCGACTGAGTTGTCTAGCGAATCACAAAAGCAGC  550
U09352    501 ATCAACGAATGATGTTTCGACTGAGTTGTCTAGCGAATCACAAAAGCAGC  550
Oklahoma  501 GTCAACGAATGATGTTTCGACTGAGTTGTCTAGCGAATCACAAAAGCAGC  550
               ************************* ***********************

12384     551 CAGAAGTACCACAAGAAGCAGTTCCAACTCCTAAAGCAGCTGAAACGACT  600
2699      551 CAGAAGTACCACAAGAAGCAGTTCCAACTCCTAAAGCAGCTGAACCGACT  600
B514      530 CAGAAGTACCACAAGAAGCAGTTCCAACTCCTAAAGCAGCTGAAACGACT  579
Spy57     551 CAGAAGTACCACAAGAAGCAGTTCCAACTCCTAAAGCAGCTGAAACGACT  600
U09352    551 CAGAAGTACCACAAGAAGCAGAACCAACTCCTAAAGCAGCTGAAAGCACT  600
Oklahoma  551 CAGAAGTACCACAAGAAGCAGTTCCAACTCCTAAAGCAGCTGAAACGACT  600
              *********************  *********************    ***

12384     601 GAAGTCGAACCTAAGACAGACATCTCAGAGGATTCAACTTCAGCTAATAG  650
2699      601 GAAGTCGAACCTAAGACAGACATCTCAGAAGACCCAACTTCAGCTAATAG  650
B514      580 GAAGTCGAACCTAAGACAGACATCTCAGAAGACCCAACTTCAGCTAATAG  629
Spy57     601 GAAGTCGAACCTAAGACAGACATCTCAGAAGCCCCAACTTCAGCTAATAG  650
U09352    601 GAAGTCGAACCTAAGACAGACATCTCAGAAGATTCAACTTCAGCTAATAG  650
Oklahoma  601 GAAGTCGAACCTAAGACAGACATCTCAGAAGCCCCAACTTCAGCTAATAG  650
              ***************************** *    ****************

12384     551 GCCTGTACCTAACGAGAGTGCTTCAGAAGAAGTTTCTTCTGCGGCCCCAG  700
2699      651 GCCTGTACCTAACGAGAGTGCTTCAGAAGAAGCTTCTTCTGCGGCCCCAG  700
B514      630 GCCTGTACCTAACGAGAGTGCTTCAGAAGAAGTTTCTTCTGCGGCCCCAG  679
Spy57     651 GCCTGTACCTAACGAGAGTGCTTCAGAAGAAGTTTCTTCTGCGGCCCCAG  700
U09352    651 GCCTGTACCTAACGGAAGTGCTTCAGAAGAAGCTTCTTCTGCGGCCCCAG  700
Oklahoma  651 GCCTGTACCTAACGAGAGTGCTTCAGAAGAAGTTTCTTCTGCGGCCCCAG  700
              **************  **************** *****************

12384     701 CACAAGCCCCAGCAGAAAAAGAAGAAACCTCT------------GCGCCA  738
2699      701 CACAAGCTCCAGCAGAAAAAGAAGAAACCTCTCAGATGTTAACTGCGCCA  750
B514      680 CACAAGCCCCAGCAGAAAAAGAAGAAACCTCT------------GCGCCA  717
Spy57     701 CACAAGCCCCAGCAGAAAAAGAAGAAACCTCT------------GCGCCA  738
U09352    701 CACAAGCTCCAGCAGAAAAAGAAGAAACCTCTCAGATGTTAACTGCGCCA  750
Oklahoma  701 CACAAGCCCCAGCAGAAAAAGAAGAAACCTCT------------GCGCCA  738
              ******* ************************            ******
```

```
12384      739  GCAGCACAAAAAGCTGTAGCTGACACCACAAGTGTTGCAACCTCAAATGG  788
2699       751  GCAGCACAAAAAGCTGTAGCTGACACCACAAGTGTTGCAACCTCAAACGG  800
B514       718  GCAGCACAAAAAGCTGTAGCTGACACCACAAGTGTTGCAACCTCAAACGG  767
Spy57      739  GCAGCACAAAAAGCTGTAGCTGACACCACAAGTGTTGCAACCTCAAATGG  788
U09352     751  GCAGCACAAAAAGCTGTAGCTGACACCACAAGTGTTGCAACCTCAAACGG  800
Oklahoma   739  GCAGCACAAAAAGCTGTAGCTGACACCACAAGTGTTGCAACCTCAAATGG  788
                *********************************************** **

12384      789  CCTTTCTTACGCTCCAAACCATGCCTACAATCCAATGAATGCAGGGCTTC  838
2699       801  CCTTTCTTACGCTCCAAACCATGCCTACAATCCAATGAATGCAGGGCTTC  850
B514       768  CCTTTCTTACGCTCCAAACCATGCCTACAATCCAATGAATGCAGGGCTTC  817
Spy57      789  CCTTTCTTACGCTCCAAACCATGCCTACAATCCAATGAATGCAGGGCTTC  838
U09352     801  CCTTTCTTACGCTCCAAACCATGCCTACAATCCAATGAATGCAGGGCTTC  850
Oklahoma   789  CCTTTCTTACGCTCCAAACCATGCCTACAATCCAATGAATGCAGGGCTTC  838
                **************************************************

12384      839  AACCACAAACAGCAGCCTTCAAAGAAGAAGTGGCTTCTGCCTTTGGTATT  888
2699       851  AACCACAAACAGCAGCCTTCAAAGAAGAAGTGGCTTCTGCCTTTGGTATT  900
B514       818  AACCACAAACAGCAGCCTTCAAAGAAGAAGTGGCTTCTGCCTTTGGTATT  867
Spy57      839  AACCACAAACAGCAGCCTTCAAAGAAGAAGTGGCTTCTGCCTTTGGTATT  888
U09352     851  AACCACAAACAGCAGCCTTCAAAGAAGAAGTG-CTTCTGCCTTTGGTATT  899
Oklahoma   839  AACCACAAACAGCAGCCTTCAAAGAAGAAGTGGCTTCTGCCTTTGGTATT  888
                ******************************** *****************

12384      889  ACGTCATTTAGTGGTTACCGTCCAGGTGATCCAGGAGATCAT-GGTAAAG  937
2699       901  ACGTCATTTAGTGGTTACCGTCCAGGAGATCCAGGAGATCAT-GGTAAAG  949
B514       868  ACGTCATTTAGTGGTTACCGTCCAGGTGACCCAGGAGATCAT-GGTAAAG  916
Spy57      889  ACGTCATTTAGTGGTTACCGTCCAGGTGATCCAGGAGATCAT-GGTAAAG  937
U09352     900  ACGTCATTTAGTGGTTACCGTCCAGGAGATCCAGGAGATCATTGGTAAAG  949
Oklahoma   889  ACGTCATTTAGTGGTTACCGTCCAGGTGATCCAGGAGATCAT-GGTAAAG  937
                ************************** ** ************ *******

12384      938  GTTTGGCCATTGATTTTATGGTGCCTGAAAATTCTGCTCTTGGTGATCAA  987
2699       950  GATTAGCCATTGACTTTATGGTACCGGTTAGCTCTACGCTTGGTGATCAA  999
B514       917  GTTTGGCCATTGATTTTATGGTGCCTGAAAATTCTGCTCTTGGTGATCAA  966
Spy57      938  GTTTGGCCATTGATTTTATGGTGCCTGAAAATTCTGCTCTTGGTGATCAA  987
U09352     950  GATTAGCCATTGACTTTATGGTACCGGTTAGCTCTACGCTTGGTGATCAA  999
Oklahoma   938  GTTTGGCCATTGATTTTATGGTGCCTGAAAATTCTGCTCTTGGTGATCAA  987
                * ** ******** ******** ** *  *  *** * ************

12384      988  GTTGCTCAATATGCCATTGACCATATGGCAGAGCGTGGTATTTCATACGT 1037
2699      1000  GTTGCTCAATATGCCATTGACCATATGGCAGAGCGTGGTATTTCATACGT 1049
B514       967  GTTGCTCAATATGCCATTGACCATATGGCAGAGCGTGGTATTTCATACGT 1016
Spy57      988  GTTGCTCAATATGCCATTGACCATATGGCAGAGCGTGGTATTTCATACGT 1037
U09352    1000  GTTGCTCAATATGCCATTGACCATATGGCAGACGGTGGTATTTCATACGT 1049
Oklahoma   988  GTTGCTCAATATGCCATTGACCATATGGCAGAGCGTGGTATTTCATACGT 1037
                ********************************  ****************

12384     1038  TATTTGGAAACAGCGATTCTATGCGCCATTTGCAAGTATTTACGGACCAG 1087
2699      1050  TATTTGGAAACAGCGATTCTATGCGCCATTTGCAAGTATTTACGGACCAG 1099
B514      1017  TATTTGGAAACAGCGATTCTATGCGCCATTTGCAAGTATTTACGGACCAG 1066
Spy57     1038  TATTTGGAAACAGCGATTCTATGCGCCATTTGCAAGTATTTACGGACCAG 1087
U09352    1050  TATTTGGAAACAGCGATTCTATGCGCCATTTGCAAGTATTTACGGACCAG 1099
Oklahoma  1038  TATTTGGAAACAGCGATTCTATGCGCCATTTGCAAGTATTTACGGACCAG 1087
                **************************************************
```

```
12384      1088 CCTACACATGGAACCCCATGCCAGATCGCGGCAGTATTACAGAAAACCAT 1137
2699       1100 CCTACACATGGAACCCCATGCCAGATCGCGGCAGTATTACAGAAAACCAT 1149
B514       1067 CTTACACATGGAACCCCATGCCAGATCGCGGCAGTATTACAGAAAACCAT 1116
Spy57      1088 CCTACACATGGAACCCCATGCCAGATCGCGGCAGTATTACAGAAAACCAT 1137
U09352     1100 CCTACACATGGAACCCCATGCCAGATCGCGGCAGTATTACAGTTTTCCAT 1149
Oklahoma   1088 CCTACACATGGAACCCCATGCCAGATCGCGGCAGTATTACAGAAAACCAT 1137
                * ****************************************    ****

12384      1138 TATGATCATGTTCATGTCTCCTTTAATGCTTAA 1170
2699       1150 TATGATCATGTTCATGTCTCCTTTAATGCTTAA 1182
B514       1117 TATGATCATGTTCATGTCTCCTTTAATGCTTAA 1149
Spy57      1138 TATGATCATGTTCATGTCTCCTTTAATGCTTAA 1170
U09352     1150 TATGATCATGTTCATGTCTCCTTTAATGCTTAA 1182
Oklahoma   1138 TATGATCATGTTCATGTCTCCTTTAATGCTTAA 1170
                *********************************
```

Figure 18

```
12384        1 MIITKKSLFVTSVALSLAPLATAQAQEWTPRSVTEIKSELVLVDNVFTYT  50
2699         1 MIITKKSLFVTSVALSLAPLATAQAQEWTPRSVTEIKSELVLVDNVFTYI  50
B514         1 MIITKKSLFVTSVALSLAPLATAQAQEWTPRSVTEIKSELVLVDNVFTYT  50
Spy57        1 MIITKKSLFVTSVALSLVPLATAQAQEWTPRSVTEIKSELVLVDNVFTYT  50
U09352       1 MIITKKSLFVTSVALSLAPLATAQAQEWTPRSVTQIKSELVLVDNVFTYT  50
Oklahoma     1 MIITKKSLFVTSVALSLVPLATAQAQEWTPRSVTEIKSELVLVDNVFTYT  50
               ***************** **************** ************** 

12384       51 VKYGDTLSTIAEAMGIDVHVLGDINHIANIDLIFPDTILTANYNQHGQAT 100
2699        51 VKYGDTLSTIAEAMGIDVHVLGDINHIANIDLIFPDTILTANYNQHGQAT 100
B514        51 VKYGDTLSTIAEAMGIDVHVLGDINHIANIDLIFPDTILTANYNQHGQAT 100
Spy57       51 VKYGDTLSTIAEAMGIDVHVLGDINHIANIDLIFPDTILTANYNQHGQAT 100
U09352      51 VKYGDTLSTIAEAMGIDVHVLGDINHIANIDLIFPDTILTANYNQHGQAT 100
Oklahoma    51 VKYGDTLSTIAEAMGIDVHVLGDINHIANIDLIFPDTILTANYNQHGQAT 100
               **************************************************

12384      101 TLTVQAPASSPASVSHVPSSEPLPQASATSQSTVPMAPSATPSDVPTTPF 150
2699       101 TLTVQAPASSPSSVSHVPSSEPLPQASATSQPTVPMAPSATPSDVPTTPF 150
B514       101 TLTVQAPASSPASVSHVPSSEPLPQASATSQPTVPMAPSATP-------L 143
Spy57      101 NLTVQAPASSPASVSHVPSSEPLPQASATSQPTVPMAPPATPSDVPTTPF 150
U09352     101 TLTVQAPASSPASVSHVPSSEPLPQASATSQSTIPMAPSATPSDVPTTPL 150
Oklahoma   101 NLTVQAPASSPASVSHVPSSEPLPQASATSQPTVPMAPPATPSDVPTTPF 150
                ********** ******************* * **** ***        

12384      151 ASAKPDSSVTASSELTSSTNDVSTELSSESQKQPEVPQEAVPTPKAAETT 200
2699       151 ASAKPDSSVTASSELTSSTNDVSTELSSESQKQPEVPQEAVPTPKAAEPT 200
B514       144 ASAKPDSSVTASSELTSSTNDVSTESSSESQKQPEVPQEAVPTPKAAETT 193
Spy57      151 ASAKPDSSVTASSELTSSTNDVSTELSSESQKQPEVPQEAVPTPKAAETT 200
U09352     151 ASAKPDSFVTASSELTSSTNDVSTELSSESQKQPEVPQEAEPTPKAAEST 200
Oklahoma   151 ASAKPDSSVTASSELTSSTNDVSTELSSESQKQPEVPQEAVPTPKAAETT 200
               ******* ***************** ************** ******* *

12384      201 EVEPKTDISEDSTSANRPVPNESASEEVSSAAPAQAPAEKE----ETSAP 246
2699       201 EVEPKTDISEDPTSANRPVPNESASEEASSAAPAQAPAEKEETSQMLTAP 250
B514       194 EVEPKTDISEDPTSANRPVPNESASEEVSSAAPAQAPAEKE----ETSAP 239
Spy57      201 EVEPKTDISEAPTSANRPVPNESASEEVSSAAPAQAPAEKE----ETSAP 246
U09352     201 EVEPKTDISEDSTSANRPVPNGSASEEASSAAPAQAPAEKEETSQMLTAP 250
Oklahoma   201 EVEPKTDISEAPTSANRPVPNESASEEVSSAAPAQAPAEKE----ETSAP 246
               **********  ********* ***** *************       **

12384      247 AAQKAVADTTSVATSNGLSYAPNHAYNPMNAGLQPQTAAFKEEVASAFGI 296
2699       251 AAQKAVADTTSVATSNGLSYAPNHAYNPMNAGLQPQTAAFKEEVASAFGI 300
B514       240 AAQKAVADTTSVATSNGLSYAPNHAYNPMNAGLQPQTAAFKEEVASAFGI 289
Spy57      247 AAQKAVADTTSVATSNGLSYAPNHAYNPMNAGLQPQTAAFKEEVASAFGI 296
U09352     251 AAQKAVADTTSVATSNGLSYAPNHAYNPMNAGLQPQTAAFKEEVLLPLVL 300
Oklahoma   247 AAQKAVADTTSVATSNGLSYAPNHAYNPMNAGLQPQTAAFKEEVASAFGI 296
               ********************************************      

12384      297 TSFSGYRPGDPGDHGKGLAIDFMVPENSALGDQVAQYAIDHMAERGISYV 346
2699       301 TSFSGYRPGDPGDHGKGLAIDFMVPVSSTLGDQVAQYAIDHMAERGISYV 350
B514       290 TSFSGYRPGDPGDHGKGLAIDFMVPENSALGDQVAQYAIDHMAERGISYV 339
Spy57      297 TSFSGYRPGDPGDHGKGLAIDFMVPENSALGDQVAQYAIDHMAERGISYV 346
U09352     301 RHLVVTVQEIQEIIGKGLAIDFMVPVSSTLGDQVAQYAIDHMADGGISYV 350
Oklahoma   297 TSFSGYRPGDPGDHGKGLAIDFMVPENSALGDQVAQYAIDHMAERGISYV 346
                             ***********  * **************  *****
```

```
12384      347 IWKQRFYAPFASIYGPAYTWNPMPDRGSITENHYDHVHVSFNA 389
2699       351 IWKQRFYAPFASIYGPAYTWNPMPDRGSITENHYDHVHVSFNA 393
B514       340 IWKQRFYAPFASIYGPAYTWNPMPDRGSITENHYDHVHVSFNA 382
Spy57      347 IWKQRFYAPFASIYGPAYTWNPMPDRGSITENHYDHVHVSFNA 389
U09352     351 IWKQRFYAPFASIYGPAYTWNPMPDRGSITVFHYDHVHVSFNA 393
Oklahoma   347 IWKQRFYAPFASIYGPAYTWNPMPDRGSITENHYDHVHVSFNA 389
               ******************************  ***********
```

Figure 19

1 ATGAAGAAAA GAATGTTATT AGCGTCAACA GTAGCCTTGT CATTTGCCCC
51 AGTATTGGCA ACTCAAGCAG AAGAAGTTCT TTGGACTGCA CGTAGTGTTG
101 AGCAAATCCA AAACGATTTG ACTAAAACGG ACAACAAAAC AAGTTATACC
151 GTACAGTATG GTGATACTTT GAGCACCATT GCAGAAGCCT TGGGTGTAGA
201 TGTCACAGTG CTTGCGAATC TGAACAAAAT CACTAATATG GACTTGATTT
251 TCCCAGAAAC TGTTTTGACA ACGACTGTCA ATGAAGCAGA AGAAGTAACA
301 GAAGTTGAAA TCCAAACACC TCAAGCAGAC TCTAGTGAAG AAGTGACAAC
351 TGCGACAGCA GATTTGACCA CTAATCAAGT GACCGTTGAT GATCAAACTG
401 TTCAGGTTGC AGACCTTTCT CAACCAATTG CAGAAGTTAC AAAGACAGTG
451 ATTGCTTCTG AAGAAGTGGC ACCATCTACG GGCACTTCTG TCCCAGAGGA
501 GCAAACGACC GAAACAACTC GCCCAGTTGA AGAAGCAACT CCTCAGGAAA
551 CGACTCCAGC TGAGAAGCAG GAAACACAAG CAAGCCCTCA AGCTGCATCA
601 GCAGTGGAAG TAACTACAAC AAGTTCAGAA GCAAAAGAAG TAGCATCATC
651 AAATGGAGCT ACAGCAGCAG TTTCTACTTA TCAACCAGAA GAGACGAAAA
701 TAATTTCAAC AACTTACGAG GCTCCAGCTG CGCCCGATTA TGCTGGACTT
751 GCAGTAGCAA AATCTGAAAA TGCAGGTCTT CAACCACAAA CAGCTGCCTT
801 TAAAGAAGAA ATTGCTAACT TGTTTGGCAT TACATCCTTT AGTGGTTATC
851 GTCCAGGAGA CAGTGGAGAT CACGGAAAAG GTTTGGCTAT CGACTTTATG
901 GTACCAGAAC GTTCAGAATT AGGGGATAAG ATTGCGGAAT ATGCTATTCA
951 AAATATGGCC AGCCGTGGCA TTAGTTACAT CATCTGGAAA CAACGTTTCT
1001 ATGCTCCATT CGATAGCAAA TATGGGCCAG CTAACACTTG GAACCCAATG
1051 CCAGACCGTG GTAGTGTGAC AGAAAATCAC TATGATCACG TTCACGTTTC
1101 AATGAATGGA TAA (SEQ ID NO:17)

Figure 20

1 MKKRMLLAST VALSFAPVLA TQAEEVLWTA RSVEQIQNDL TKTDNKTSYT
51 VQYGDTLSTI AEALGVDVTV LANLNKITNM DLIFPETVLT TTVNEAEEVT
101 EVEIQTPQAD SSEEVTTATA DLTTNQVTVD DQTVQVADLS QPIAEVTKTV
151 IASEEVAPST GTSVPEEQTT ETTRPVEEAT PQETTPAEKQ ETQASPQAAS
201 AVEVTTTSSE AKEVASSNGA TAAVSTYQPE ETKIISTTYE APAAPDYAGL
251 AVAKSENAGL QPQTAAFKEE IANLFGITSF SGYRPGDSGD HGKGLAIDFM
301 VPERSELGDK IAEYAIQNMA SRGISYIIWK QRFYAPFDSK YGPANTWNPM
351 PDRGSVTENH YDHVHVSMNG * (SEQ ID NO:18)

SEQUENCE LISTING

```
<160> NUMBER OF SEQ ID NOS: 29

<210> SEQ ID NO 1
<211> LENGTH: 1170
<212> TYPE: DNA
<213> ORGANISM: S. pyogenes

<400> SEQUENCE: 1

atgattatta ctaaaaagag cttatttgtg acaagtgtcg ctttgtcgtt agcacctttg     60

gcgacagcac aggcacaaga gtggacacca cgatcggtta cagaaatcaa gtctgaactc    120

gtcctagttg ataatgtttt tacttatact gtaaaatacg gtgacacttt aagcacaatt    180

gctgaagcaa tgggaattga tgtgcatgtc ttaggagata ttaatcatat tgctaatatt    240

gacttaattt ttccagacac gatcctaaca gccaactaca accaacacgg tcaggcaacg    300

actttgacgg ttcaagcgcc tgcttctagt ccagctagcg ttagtcatgt acctagcagt    360

gagccattac cccaagcatc tgccacctct caatcgactg ttcctatggc accatctgcg    420

acaccatctg atgtcccaac gacaccattc gcatctgcaa agccagatag ttctgtgaca    480

gcgtcatctg agctcacatc gtcaacgaat gatgtttcga ctgagttgtc tagcgaatca    540

caaaagcagc cagaagtacc acaagaagca gttccaactc ctaaagcagc tgaaacgact    600

gaagtcgaac ctaagacaga catctcagag gattcaactt cagctaatag gcctgtacct    660

aacgagagtg cttcagaaga agtttcttct gcggccccag cacaagcccc agcagaaaaa    720

gaagaaacct ctgcgccagc agcacaaaaa gctgtagctg acaccacaag tgttgcaacc    780

tcaaatggcc tttcttacgc tccaaaccat gcctacaatc caatgaatgc agggcttcaa    840

ccacaaacag cagccttcaa agaagaagtg gcttctgcct ttggtattac gtcatttagt    900

ggttaccgtc caggtgatcc aggagatcat ggtaaaggtt tggccattga ttttatggtg    960

cctgaaaatt ctgctcttgg tgatcaagtt gctcaatatg ccattgacca tatggcagag   1020

cgtggtattt catacgttat ttggaaacag cgattctatg cgccatttgc aagtatttac   1080

ggaccagcct acacatggaa ccccatgcca gatcgcggca gtattacaga aaaccattat   1140
```

-continued

```
gatcatgttc atgtctcctt taatgcttaa                                        1170


<210> SEQ ID NO 2
<211> LENGTH: 389
<212> TYPE: PRT
<213> ORGANISM: S. pyogenes

<400> SEQUENCE: 2

Met Ile Ile Thr Lys Lys Ser Leu Phe Val Thr Ser Val Ala Leu Ser
 1               5                  10                  15

Leu Ala Pro Leu Ala Thr Ala Gln Ala Gln Glu Trp Thr Pro Arg Ser
            20                  25                  30

Val Thr Glu Ile Lys Ser Glu Leu Val Leu Val Asp Asn Val Phe Thr
        35                  40                  45

Tyr Thr Val Lys Tyr Gly Asp Thr Leu Ser Thr Ile Ala Glu Ala Met
    50                  55                  60

Gly Ile Asp Val His Val Leu Gly Asp Ile Asn His Ile Ala Asn Ile
65                  70                  75                  80

Asp Leu Ile Phe Pro Asp Thr Ile Leu Thr Ala Asn Tyr Asn Gln His
                85                  90                  95

Gly Gln Ala Thr Thr Leu Thr Val Gln Ala Pro Ala Ser Ser Pro Ala
            100                 105                 110

Ser Val Ser His Val Pro Ser Ser Glu Pro Leu Pro Gln Ala Ser Ala
        115                 120                 125

Thr Ser Gln Ser Thr Val Pro Met Ala Pro Ser Ala Thr Pro Ser Asp
    130                 135                 140

Val Pro Thr Thr Pro Phe Ala Ser Ala Lys Pro Asp Ser Ser Val Thr
145                 150                 155                 160

Ala Ser Ser Glu Leu Thr Ser Ser Thr Asn Asp Val Ser Thr Glu Leu
                165                 170                 175

Ser Ser Glu Ser Gln Lys Gln Pro Glu Val Pro Gln Glu Ala Val Pro
            180                 185                 190

Thr Pro Lys Ala Ala Glu Thr Thr Glu Val Glu Pro Lys Thr Asp Ile
        195                 200                 205

Ser Glu Asp Ser Thr Ser Ala Asn Arg Pro Val Pro Asn Glu Ser Ala
    210                 215                 220

Ser Glu Glu Val Ser Ser Ala Ala Pro Ala Gln Ala Pro Ala Glu Lys
225                 230                 235                 240

Glu Glu Thr Ser Ala Pro Ala Ala Gln Lys Ala Val Ala Asp Thr Thr
                245                 250                 255

Ser Val Ala Thr Ser Asn Gly Leu Ser Tyr Ala Pro Asn His Ala Tyr
            260                 265                 270

Asn Pro Met Asn Ala Gly Leu Gln Pro Gln Thr Ala Ala Phe Lys Glu
        275                 280                 285

Glu Val Ala Ser Ala Phe Gly Ile Thr Ser Phe Ser Gly Tyr Arg Pro
    290                 295                 300

Gly Asp Pro Gly Asp His Gly Lys Gly Leu Ala Ile Asp Phe Met Val
305                 310                 315                 320

Pro Glu Asn Ser Ala Leu Gly Asp Gln Val Ala Gln Tyr Ala Ile Asp
                325                 330                 335

His Met Ala Glu Arg Gly Ile Ser Tyr Val Ile Trp Lys Gln Arg Phe
            340                 345                 350

Tyr Ala Pro Phe Ala Ser Ile Tyr Gly Pro Ala Tyr Thr Trp Asn Pro
        355                 360                 365
```

-continued

Met Pro Asp Arg Gly Ser Ile Thr Glu Asn His Tyr Asp His Val His
370 375 380

Val Ser Phe Asn Ala
385

<210> SEQ ID NO 3
<211> LENGTH: 1182
<212> TYPE: DNA
<213> ORGANISM: S. pyogenes

<400> SEQUENCE: 3
atgattatta ctaaaaagag cttatttgtg acaagtgtcg ctttgtcgtt agcacctttg 60
gcgacagcgc aggcacaaga gtggacacca cgatcggtta cagaaatcaa gtctgaactc 120
gtcctagttg ataatgtttt tacttatata gtaaaatacg gtgacacttt aagcacaatt 180
gctgaagcaa tggggattga tgtgcatgtc ttaggagata ttaatcatat tgctaatatt 240
gacttaattt ttccagacac gatcctaaca gcaaactaca accaacacgg tcaggcaacg 300
actttgacgg ttcaagcacc tgcttctagt ccatctagcg ttagtcatgt acctagcagt 360
gagccattac cccaagcatc tgccacctct caaccgactg ttcctatggc accatctgcg 420
acaccatctg atgtcccaac gacaccattc gcatctgcaa agccagatag ttctgtgaca 480
gcgtcatctg agctcacatc gtcaacgaat gatgtttcga ctgagttgtc tagcgaatca 540
caaaagcagc cagaagtacc acaagaagca gttccaactc ctaaagcagc tgaaccgact 600
gaagtcgaac ctaagacaga catctcagaa gacccaactt cagctaatag gcctgtacct 660
aacgagagtg cttcagaaga agcttcttct gcggccccag cacaagctcc agcagaaaaa 720
gaagaaacct ctcagatgtt aactgcgcca gcagcacaaa aagctgtagc tgacaccaca 780
agtgttgcaa cctcaaacgg cctttcttac gctccaaacc atgcctacaa tccaatgaat 840
gcagggcttc aaccacaaac agcagccttc aaagaagaag tggcttctgc ctttggtatt 900
acgtcattta gtggttaccg tccaggagat ccaggagatc atggtaaagg attagccatt 960
gactttatgg taccggttag ctctacgctt ggtgatcaag ttgctcaata tgccattgac 020
catatggcag agcgtggtat ttcatacgtt atttggaaac agcgattcta tgcgccattt 080
gcaagtattt acggaccagc ctacacatgg aaccccatgc cagatcgcgg cagtattaca 140
gaaaaccatt atgatcatgt tcatgtctcc tttaatgctt aa 182

<210> SEQ ID NO 4
<211> LENGTH: 393
<212> TYPE: PRT
<213> ORGANISM: S. pyogenes

<400> SEQUENCE: 4

Met Ile Ile Thr Lys Lys Ser Leu Phe Val Thr Ser Val Ala Leu Ser
1 5 10 15

Leu Ala Pro Leu Ala Thr Ala Gln Ala Gln Glu Trp Thr Pro Arg Ser
20 25 30

Val Thr Glu Ile Lys Ser Glu Leu Val Leu Val Asp Asn Val Phe Thr
35 40 45

Tyr Ile Val Lys Tyr Gly Asp Thr Leu Ser Thr Ile Ala Glu Ala Met
50 55 60

Gly Ile Asp Val His Val Leu Gly Asp Ile Asn His Ile Ala Asn Ile
65 70 75 80

Asp Leu Ile Phe Pro Asp Thr Ile Leu Thr Ala Asn Tyr Asn Gln His

-continued

```
                85                  90                  95

Gly Gln Ala Thr Thr Leu Thr Val Gln Ala Pro Ala Ser Ser Pro Ser
            100                 105                 110

Ser Val Ser His Val Pro Ser Ser Glu Pro Leu Pro Gln Ala Ser Ala
        115                 120                 125

Thr Ser Gln Pro Thr Val Pro Met Ala Pro Ser Ala Thr Pro Ser Asp
    130                 135                 140

Val Pro Thr Thr Pro Phe Ala Ser Ala Lys Pro Asp Ser Ser Val Thr
145                 150                 155                 160

Ala Ser Ser Glu Leu Thr Ser Ser Thr Asn Asp Val Ser Thr Glu Leu
                165                 170                 175

Ser Ser Glu Ser Gln Lys Gln Pro Glu Val Pro Gln Glu Ala Val Pro
            180                 185                 190

Thr Pro Lys Ala Ala Glu Pro Thr Glu Val Glu Pro Lys Thr Asp Ile
        195                 200                 205

Ser Glu Asp Pro Thr Ser Ala Asn Arg Pro Val Pro Asn Glu Ser Ala
    210                 215                 220

Ser Glu Glu Ala Ser Ser Ala Ala Pro Ala Gln Ala Pro Ala Glu Lys
225                 230                 235                 240

Glu Glu Thr Ser Gln Met Leu Thr Ala Pro Ala Ala Gln Lys Ala Val
                245                 250                 255

Ala Asp Thr Thr Ser Val Ala Thr Ser Asn Gly Leu Ser Tyr Ala Pro
            260                 265                 270

Asn His Ala Tyr Asn Pro Met Asn Ala Gly Leu Gln Pro Gln Thr Ala
        275                 280                 285

Ala Phe Lys Glu Glu Val Ala Ser Ala Phe Gly Ile Thr Ser Phe Ser
    290                 295                 300

Gly Tyr Arg Pro Gly Asp Pro Gly Asp His Gly Lys Gly Leu Ala Ile
305                 310                 315                 320

Asp Phe Met Val Pro Val Ser Ser Thr Leu Gly Asp Gln Val Ala Gln
                325                 330                 335

Tyr Ala Ile Asp His Met Ala Glu Arg Gly Ile Ser Tyr Val Ile Trp
            340                 345                 350

Lys Gln Arg Phe Tyr Ala Pro Phe Ala Ser Ile Tyr Gly Pro Ala Tyr
        355                 360                 365

Thr Trp Asn Pro Met Pro Asp Arg Gly Ser Ile Thr Glu Asn His Tyr
    370                 375                 380

Asp His Val His Val Ser Phe Asn Ala
385                 390
```

<210> SEQ ID NO 5
<211> LENGTH: 1170
<212> TYPE: DNA
<213> ORGANISM: S. pyogenes

<400> SEQUENCE: 5

```
atgattatta ctaaaaagag cttatttgtg acaagtgtcg ctttgtcgtt agtacctttg     60

gcgacagcgc aggcacaaga gtggacacca cgatcggtta cagaaatcaa gtctgaactc    120

gtcctagttg ataatgtttt tacttatact gtaaaatacg gtgacacttt aagcacaatt    180

gctgaagcaa tggggattga tgtgcatgtc ttaggagata ttaatcatat tgctaatatt    240

gacctaattt ttccagacac gatcctaaca gcaaactaca atcaacacgg tcaggcaacg    300

aatttgacgg ttcaagcacc tgcttctagt ccagctagcg ttagtcatgt acctagcagt    360
```

-continued

```
gagccattac cccaagcatc tgccacctct caaccgactg ttcctatggc accacctgcg    420

acaccatctg atgtcccaac gacaccattc gcatctgcaa agccagatag ttctgtgaca    480

gcgtcatctg agctcacatc gtcaacgaat gatgtttcga ctgagttgtc tagcgaatca    540

caaaagcagc cagaagtacc acaagaagca gttccaactc ctaaagcagc tgaaacgact    600

gaagtcgaac ctaagacaga catctcagaa gccccaactt cagctaatag gcctgtacct    660

aacgagagtg cttcagaaga agtttcttct gcggccccag cacaagcccc agcagaaaaa    720

gaagaaacct ctgcgccagc agcacaaaaa gctgtagctg acaccacaag tgttgcaacc    780

tcaaatggcc tttcttacgc tccaaaccat gcctacaatc caatgaatgc agggcttcaa    840

ccacaaacag cagccttcaa agaagaagtg gcttctgcct ttggtattac gtcatttagt    900

ggttaccgtc caggtgatcc aggagatcat ggtaaaggtt tggccattga ttttatggtg    960

cgtggtattt catacgttat ttggaaacag cgattctatg cgccatttgc aagtatttac   1080

ggaccagcct acacatggaa ccccatgcca gatcgcggca gtattacaga aaaccattat   1140

gatcatgttc atgtctcctt taatgcttaa                                     1170
```

<210> SEQ ID NO 6
<211> LENGTH: 389
<212> TYPE: PRT
<213> ORGANISM: S. pyogenes

<400> SEQUENCE: 6

```
Met Ile Ile Thr Lys Lys Ser Leu Phe Val Thr Ser Val Ala Leu Ser
 1               5                  10                  15

Leu Val Pro Leu Ala Thr Ala Gln Ala Gln Glu Trp Thr Pro Arg Ser
            20                  25                  30

Val Thr Glu Ile Lys Ser Glu Leu Val Leu Val Asp Asn Val Phe Thr
        35                  40                  45

Tyr Thr Val Lys Tyr Gly Asp Thr Leu Ser Thr Ile Ala Glu Ala Met
    50                  55                  60

Gly Ile Asp Val His Val Leu Gly Asp Ile Asn His Ile Ala Asn Ile
65                  70                  75                  80

Asp Leu Ile Phe Pro Asp Thr Ile Leu Thr Ala Asn Tyr Asn Gln His
                85                  90                  95

Gly Gln Ala Thr Asn Leu Thr Val Gln Ala Pro Ala Ser Ser Pro Ala
            100                 105                 110

Ser Val Ser His Val Pro Ser Ser Glu Pro Leu Pro Gln Ala Ser Ala
        115                 120                 125

Thr Ser Gln Pro Thr Val Pro Met Ala Pro Pro Ala Thr Pro Ser Asp
    130                 135                 140

Val Pro Thr Thr Pro Phe Ala Ser Ala Lys Pro Asp Ser Ser Val Thr
145                 150                 155                 160

Ala Ser Ser Glu Leu Thr Ser Ser Thr Asn Asp Val Ser Thr Glu Leu
                165                 170                 175

Ser Ser Glu Ser Gln Lys Gln Pro Glu Val Pro Gln Glu Ala Val Pro
            180                 185                 190

Thr Pro Lys Ala Ala Glu Thr Thr Glu Val Glu Pro Lys Thr Asp Ile
        195                 200                 205

Ser Glu Ala Pro Thr Ser Ala Asn Arg Pro Val Pro Asn Glu Ser Ala
    210                 215                 220

Ser Glu Glu Val Ser Ser Ala Ala Pro Ala Gln Ala Pro Ala Glu Lys
225                 230                 235                 240
```

-continued

```
Glu Glu Thr Ser Ala Pro Ala Ala Gln Lys Ala Val Ala Asp Thr Thr
                245                 250                 255

Ser Val Ala Thr Ser Asn Gly Leu Ser Tyr Ala Pro Asn His Ala Tyr
            260                 265                 270

Asn Pro Met Asn Ala Gly Leu Gln Pro Gln Thr Ala Ala Phe Lys Glu
        275                 280                 285

Glu Val Ala Ser Ala Phe Gly Ile Thr Ser Phe Ser Gly Tyr Arg Pro
    290                 295                 300

Gly Asp Pro Gly Asp His Gly Lys Gly Leu Ala Ile Asp Phe Met Val
305                 310                 315                 320

Pro Glu Asn Ser Ala Leu Gly Asp Gln Val Ala Gln Tyr Ala Ile Asp
                325                 330                 335

His Met Ala Glu Arg Gly Ile Ser Tyr Val Ile Trp Lys Gln Arg Phe
            340                 345                 350

Tyr Ala Pro Phe Ala Ser Ile Tyr Gly Pro Ala Tyr Thr Trp Asn Pro
        355                 360                 365

Met Pro Asp Arg Gly Ser Ile Thr Glu Asn His Tyr Asp His Val His
    370                 375                 380

Val Ser Phe Asn Ala
385


<210> SEQ ID NO 7
<211> LENGTH: 1149
<212> TYPE: DNA
<213> ORGANISM: S. pyogenes

<400> SEQUENCE: 7

atgattatta ctaaaaagag cttatttgtg acaagtgtcg ctttgtcgtt agcacctttg      60

gcgacagcgc aggcacaaga gtggacacca cgatcggtta cagaaatcaa gtctgaactc     120

gtcctagttg ataatgtttt tacttataca gtaaaatacg gtgacacttt aagcacaatt     180

gctgaagcaa tggggattga tgtgcatgtc ttaggagata ttaatcatat tgctaatatt     240

gacttaattt ttccagacac gatcctaaca gcaaactaca atcaacacgg tcaggcaacg     300

actttgacgg ttcaagcacc tgcttctagt ccagctagcg ttagtcatgt acctagcagt     360

gagccattac cccaagcatc tgccacctct caaccgactg ttcctatggc accatctgcg     420

acaccattag catctgcaaa gccagatagt tctgtgacag cgtcatctga gctcacatcg     480

tcaacgaatg atgtttcgac tgagtcgtct agcgaatcac aaaagcagcc agaagtacca     540

caagaagcag ttccaactcc taaagcagct gaaacgactg aagtcgaacc taagacagac     600

atctcagaag acccaacttc agctaatagg cctgtaccta acgagagtgc ttcagaagaa     660

gtttcttctg cggccccagc acaagcccca gcagaaaaag aagaaacctc tgcgccagca     720

gcacaaaaag ctgtagctga caccacaagt gttgcaacct caaacggcct ttcttacgct     780

ccaaaccatg cctacaatcc aatgaatgca gggcttcaac cacaaacagc agccttcaaa     840

gaagaagtgg cttctgcctt tggtattacg tcatttagtg gttaccgtcc aggtgaccca     900

ggagatcatg gtaaaggttt ggccattgat tttatggtgc ctgaaaattc tgctcttggt     960

gatcaagttg ctcaatatgc cattgaccat atggcagagc gtggtatttc atacgttatt    1020

tggaaacagc gattctatgc gccatttgca agtatttacg gaccagctta cacatggaac    1080

cccatgccag atcgcggcag tattacagaa aaccattatg atcatgttca tgtctccttt    1140

aatgcttaa                                                            1149
```

```
<210> SEQ ID NO 8
<211> LENGTH: 382
<212> TYPE: PRT
<213> ORGANISM: S. pyogenes

<400> SEQUENCE: 8

Met Ile Ile Thr Lys Lys Ser Leu Phe Val Thr Ser Val Ala Leu Ser
 1               5                  10                  15

Leu Ala Pro Leu Ala Thr Ala Gln Ala Gln Glu Trp Thr Pro Arg Ser
            20                  25                  30

Val Thr Glu Ile Lys Ser Glu Leu Val Leu Val Asp Asn Val Phe Thr
        35                  40                  45

Tyr Thr Val Lys Tyr Gly Asp Thr Leu Ser Thr Ile Ala Glu Ala Met
    50                  55                  60

Gly Ile Asp Val His Val Leu Gly Asp Ile Asn His Ile Ala Asn Ile
65                  70                  75                  80

Asp Leu Ile Phe Pro Asp Thr Ile Leu Thr Ala Asn Tyr Asn Gln His
                85                  90                  95

Gly Gln Ala Thr Thr Leu Thr Val Gln Ala Pro Ala Ser Ser Pro Ala
            100                 105                 110

Ser Val Ser His Val Pro Ser Ser Glu Pro Leu Pro Gln Ala Ser Ala
        115                 120                 125

Thr Ser Gln Pro Thr Val Pro Met Ala Pro Ser Ala Thr Pro Leu Ala
    130                 135                 140

Ser Ala Lys Pro Asp Ser Ser Val Thr Ala Ser Ser Glu Leu Thr Ser
145                 150                 155                 160

Ser Thr Asn Asp Val Ser Thr Glu Ser Ser Ser Glu Ser Gln Lys Gln
                165                 170                 175

Pro Glu Val Pro Gln Glu Ala Val Pro Thr Pro Lys Ala Ala Glu Thr
            180                 185                 190

Thr Glu Val Glu Pro Lys Thr Asp Ile Ser Glu Asp Pro Thr Ser Ala
        195                 200                 205

Asn Arg Pro Val Pro Asn Glu Ser Ala Ser Glu Glu Val Ser Ser Ala
    210                 215                 220

Ala Pro Ala Gln Ala Pro Ala Glu Lys Glu Glu Thr Ser Ala Pro Ala
225                 230                 235                 240

Ala Gln Lys Ala Val Ala Asp Thr Thr Ser Val Ala Thr Ser Asn Gly
                245                 250                 255

Leu Ser Tyr Ala Pro Asn His Ala Tyr Asn Pro Met Asn Ala Gly Leu
            260                 265                 270

Gln Pro Gln Thr Ala Ala Phe Lys Glu Glu Val Ala Ser Ala Phe Gly
        275                 280                 285

Ile Thr Ser Phe Ser Gly Tyr Arg Pro Gly Asp Pro Gly Asp His Gly
    290                 295                 300

Lys Gly Leu Ala Ile Asp Phe Met Val Pro Glu Asn Ser Ala Leu Gly
305                 310                 315                 320

Asp Gln Val Ala Gln Tyr Ala Ile Asp His Met Ala Glu Arg Gly Ile
                325                 330                 335

Ser Tyr Val Ile Trp Lys Gln Arg Phe Tyr Ala Pro Phe Ala Ser Ile
            340                 345                 350

Tyr Gly Pro Ala Tyr Thr Trp Asn Pro Met Pro Asp Arg Gly Ser Ile
        355                 360                 365

Thr Glu Asn His Tyr Asp His Val His Val Ser Phe Asn Ala
    370                 375                 380
```

<210> SEQ ID NO 9
<211> LENGTH: 1095
<212> TYPE: DNA
<213> ORGANISM: S. pyogenes

<400> SEQUENCE: 9

```
caagagtgga caccacgatc ggttacagaa atcaagtctg aactcgtcct agttgataat     60

gtttttactt atactgtaaa atacggtgac actttaagca caattgctga agcaatggga    120

attgatgtgc atgtcttagg agatattaat catattgcta atattgactt aatttttcca    180

gacacgatcc taacagccaa ctacaaccaa cacggtcagg caacgacttt gacggttcaa    240

gcgcctgctt ctagtccagc tagcgttagt catgtaccta gcagtgagcc attaccccaa    300

gcatctgcca cctctcaatc gactgttcct atggcaccat ctgcgacacc atctgatgtc    360

ccaacgacac cattcgcatc tgcaaagcca gatagttctg tgacagcgtc atctgagctc    420

acatcgtcaa cgaatgatgt ttcgactgag ttgtctagcg aatcacaaaa gcagccagaa    480

gtaccacaag aagcagttcc aactcctaaa gcagctgaaa cgactgaagt cgaacctaag    540

acagacatct cagaggattc aacttcagct aataggcctg tacctaacga gagtgcttca    600

gaagaagttt cttctgcggc cccagcacaa gccccagcag aaaaagaaga aacctctgcg    660

ccagcagcac aaaaagctgt agctgacacc acaagtgttg caacctcaaa tggcctttct    720

tacgctccaa accatgccta caatccaatg aatgcagggc ttcaaccaca aacagcagcc    780

ttcaaagaag aagtggcttc tgcctttggt attacgtcat ttagtggtta ccgtccaggt    840

gatccaggag atcatggtaa aggtttggcc attgatttta tggtgcctga aaattctgct    900

cttggtgatc aagttgctca atatgccatt gaccatatgg cagagcgtgg tatttcatac    960

gttatttgga aacagcgatt ctatgcgcca tttgcaagta tttacggacc agcctacaca   1020

tggaacccca tgccagatcg cggcagtatt acagaaaacc attatgatca tgttcatgtc   1080

tcctttaatg cttaa                                                     1095
```

<210> SEQ ID NO 10
<211> LENGTH: 364
<212> TYPE: PRT
<213> ORGANISM: S. pyogenes

<400> SEQUENCE: 10

```
Gln Glu Trp Thr Pro Arg Ser Val Thr Glu Ile Lys Ser Glu Leu Val
 1               5                  10                  15

Leu Val Asp Asn Val Phe Thr Tyr Thr Val Lys Tyr Gly Asp Thr Leu
            20                  25                  30

Ser Thr Ile Ala Glu Ala Met Gly Ile Asp Val His Val Leu Gly Asp
        35                  40                  45

Ile Asn His Ile Ala Asn Ile Asp Leu Ile Phe Pro Asp Thr Ile Leu
    50                  55                  60

Thr Ala Asn Tyr Asn Gln His Gly Gln Ala Thr Thr Leu Thr Val Gln
65                  70                  75                  80

Ala Pro Ala Ser Ser Pro Ala Ser Val Ser His Val Pro Ser Ser Glu
                85                  90                  95

Pro Leu Pro Gln Ala Ser Ala Thr Ser Gln Ser Thr Val Pro Met Ala
            100                 105                 110

Pro Ser Ala Thr Pro Ser Asp Val Pro Thr Thr Pro Phe Ala Ser Ala
        115                 120                 125

Lys Pro Asp Ser Ser Val Thr Ala Ser Ser Glu Leu Thr Ser Ser Thr
```

-continued

```
    130                 135                 140

Asn Asp Val Ser Thr Glu Leu Ser Ser Glu Ser Gln Lys Gln Pro Glu
145                 150                 155                 160

Val Pro Gln Glu Ala Val Pro Thr Pro Lys Ala Ala Glu Thr Thr Glu
                165                 170                 175

Val Glu Pro Lys Thr Asp Ile Ser Glu Asp Ser Thr Ser Ala Asn Arg
            180                 185                 190

Pro Val Pro Asn Glu Ser Ala Ser Glu Glu Val Ser Ser Ala Ala Pro
        195                 200                 205

Ala Gln Ala Pro Ala Glu Lys Glu Glu Thr Ser Ala Pro Ala Ala Gln
    210                 215                 220

Lys Ala Val Ala Asp Thr Thr Ser Val Ala Thr Ser Asn Gly Leu Ser
225                 230                 235                 240

Tyr Ala Pro Asn His Ala Tyr Asn Pro Met Asn Ala Gly Leu Gln Pro
                245                 250                 255

Gln Thr Ala Ala Phe Lys Glu Glu Val Ala Ser Ala Phe Gly Ile Thr
            260                 265                 270

Ser Phe Ser Gly Tyr Arg Pro Gly Asp Pro Gly Asp His Gly Lys Gly
        275                 280                 285

Leu Ala Ile Asp Phe Met Val Pro Glu Asn Ser Ala Leu Gly Asp Gln
    290                 295                 300

Val Ala Gln Tyr Ala Ile Asp His Met Ala Glu Arg Gly Ile Ser Tyr
305                 310                 315                 320

Val Ile Trp Lys Gln Arg Phe Tyr Ala Pro Phe Ala Ser Ile Tyr Gly
                325                 330                 335

Pro Ala Tyr Thr Trp Asn Pro Met Pro Asp Arg Gly Ser Ile Thr Glu
            340                 345                 350

Asn His Tyr Asp His Val His Val Ser Phe Asn Ala
        355                 360
```

<210> SEQ ID NO 11
<211> LENGTH: 1106
<212> TYPE: DNA
<213> ORGANISM: S. pyogenes

<400> SEQUENCE: 11

```
caagagtgga caccacgatc ggttacagaa atcaagtctg aactcgtcct agttgataat     60

gtttttactt atatagtaaa atacggtgac actttaagca caattgctga agcaatgggg    120

attgatgtgc atgtcttagg agatattaat catattgcta atattgactt aatttttcca    180

gacacgatcc taacagcaaa ctacaaccaa cacggtcagg caacgacttt gacggttcaa    240

gcacctgctt ctagtccatc tagcgttagt catgtaccta gcagtgagcc attaccccaa    300

gcatctgcca cctctcaacc gactgttcct atggcaccat ctgcgacacc atctgatgtc    360

ccaacgacac cattcgcatc tgcaaagcca gatagttctg tgacagcgtc atctgagctc    420

acatcgtcaa cgaatgatgt ttcgactgag ttgtctagcg aatcacaaaa gcagccagaa    480

gtaccacaag aagcagttcc aactcctaaa gcagctgaac cgactgaagt cgaacctaag    540

acagacatct cagaagaccc aacttcagct aataggcctg acctaacgag agtgcttcag    600

aagaagcttc ttctgcggcc ccagcacaag ctccagcaga aaaagaagaa acctctcaga    660

tgttaactgc gccagcagca caaaaagctg tagctgacac cacaagtgtt gcaacctcaa    720

acggcctttc ttacgctcca aaccatgcct acaatccaat gaatgcaggg cttcaaccac    780

aaacagcagc cttcaaagaa gaagtggctt ctgcctttgg tattacgtca tttagtggtt    840
```

```
accgtccagg agatccagga gatcatggta aaggattagc cattgacttt atggtaccgg    900

ttagctctac gcttggtgat caagttgctc aatatgccat tgaccatatg gcagagcgtg    960

gtatttcata cgttatttgg aaacagcgat tctatgcgcc atttgcaagt atttacggac   1020

cagcctacac atggaacccc atgccagatc gcggcagtat tacagaaaac cattatgatc   1080

atgttcatgt ctcctttaat gcttaa                                        1106


<210> SEQ ID NO 12
<211> LENGTH: 368
<212> TYPE: PRT
<213> ORGANISM: S. pyogenes

<400> SEQUENCE: 12

Gln Glu Trp Thr Pro Arg Ser Val Thr Glu Ile Lys Ser Glu Leu Val
 1               5                  10                  15

Leu Val Asp Asn Val Phe Thr Tyr Ile Val Lys Tyr Gly Asp Thr Leu
            20                  25                  30

Ser Thr Ile Ala Glu Ala Met Gly Ile Asp Val His Val Leu Gly Asp
        35                  40                  45

Ile Asn His Ile Ala Asn Ile Asp Leu Ile Phe Pro Asp Thr Ile Leu
    50                  55                  60

Thr Ala Asn Tyr Asn Gln His Gly Gln Ala Thr Thr Leu Thr Val Gln
65                  70                  75                  80

Ala Pro Ala Ser Ser Pro Ser Ser Val Ser His Val Pro Ser Ser Glu
                85                  90                  95

Pro Leu Pro Gln Ala Ser Ala Thr Ser Gln Pro Thr Val Pro Met Ala
            100                 105                 110

Pro Ser Ala Thr Pro Ser Asp Val Pro Thr Thr Pro Phe Ala Ser Ala
        115                 120                 125

Lys Pro Asp Ser Ser Val Thr Ala Ser Ser Glu Leu Thr Ser Ser Thr
    130                 135                 140

Asn Asp Val Ser Thr Glu Leu Ser Ser Glu Ser Gln Lys Gln Pro Glu
145                 150                 155                 160

Val Pro Gln Glu Ala Val Pro Thr Pro Lys Ala Ala Glu Pro Thr Glu
                165                 170                 175

Val Glu Pro Lys Thr Asp Ile Ser Glu Asp Pro Thr Ser Ala Asn Arg
            180                 185                 190

Pro Val Pro Asn Glu Ser Ala Ser Glu Glu Ala Ser Ser Ala Ala Pro
        195                 200                 205

Ala Gln Ala Pro Ala Glu Lys Glu Glu Thr Ser Gln Met Leu Thr Ala
    210                 215                 220

Pro Ala Ala Gln Lys Ala Val Ala Asp Thr Thr Ser Val Ala Thr Ser
225                 230                 235                 240

Asn Gly Leu Ser Tyr Ala Pro Asn His Ala Tyr Asn Pro Met Asn Ala
                245                 250                 255

Gly Leu Gln Pro Gln Thr Ala Ala Phe Lys Glu Glu Val Ala Ser Ala
            260                 265                 270

Phe Gly Ile Thr Ser Phe Ser Gly Tyr Arg Pro Gly Asp Pro Gly Asp
        275                 280                 285

His Gly Lys Gly Leu Ala Ile Asp Phe Met Val Pro Val Ser Ser Thr
    290                 295                 300

Leu Gly Asp Gln Val Ala Gln Tyr Ala Ile Asp His Met Ala Glu Arg
305                 310                 315                 320
```

-continued

```
Gly Ile Ser Tyr Val Ile Trp Lys Gln Arg Phe Tyr Ala Pro Phe Ala
                325                 330                 335

Ser Ile Tyr Gly Pro Ala Tyr Thr Trp Asn Pro Met Pro Asp Arg Gly
            340                 345                 350

Ser Ile Thr Glu Asn His Tyr Asp His Val His Val Ser Phe Asn Ala
        355                 360                 365
```

<210> SEQ ID NO 13
<211> LENGTH: 1095
<212> TYPE: DNA
<213> ORGANISM: S. pyogenes

<400> SEQUENCE: 13

```
caagagtgga caccacgatc ggttacagaa atcaagtctg aactcgtcct agttgataat     60

gtttttactt atactgtaaa atacggtgac actttaagca caattgctga agcaatgggg    120

attgatgtgc atgtcttagg agatattaat catattgcta atattgacct aatttttcca    180

gacacgatcc taacagcaaa ctacaatcaa cacggtcagg caacgaattt gacggttcaa    240

gcacctgctt ctagtccagc tagcgttagt catgtaccta gcagtgagcc attaccccaa    300

gcatctgcca cctctcaacc gactgttcct atggcaccac ctgcgacacc atctgatgtc    360

ccaacgacac cattcgcatc tgcaaagcca gatagttctg tgacagcgtc atctgagctc    420

acatcgtcaa cgaatgatgt ttcgactgag ttgtctagcg aatcacaaaa gcagccagaa    480

gtaccacaag aagcagttcc aactcctaaa gcagctgaaa cgactgaagt cgaacctaag    540

acagacatct cagaagcccc aacttcagct aataggcctg tacctaacga gagtgcttca    600

gaagaagttt cttctgcggc cccagcacaa gccccagcag aaaaagaaga aacctctgcg    660

ccagcagcac aaaaagctgt agctgacacc acaagtgttg caacctcaaa tggcctttct    720

tacgctccaa accatgccta caatccaatg aatgcagggc ttcaaccaca aacagcagcc    780

ttcaaagaag aagtggcttc tgcctttggt attacgtcat ttagtggtta ccgtccaggt    840

gatccaggag atcatggtaa aggtttggcc attgatttta tggtgcctga aaattctgct    900

cttggtgatc aagttgctca atatgccatt gaccatatgg cagagcgtgg tatttcatac    960

gttatttgga aacagcgatt ctatgcgcca tttgcaagta tttacggacc agcctacaca   1020

tggaacccca tgccagatcg cggcagtatt acagaaaacc attatgatca tgttcatgtc   1080

tcctttaatg cttaa                                                     1095
```

<210> SEQ ID NO 14
<211> LENGTH: 364
<212> TYPE: PRT
<213> ORGANISM: S. pyogenes

<400> SEQUENCE: 14

```
Gln Glu Trp Thr Pro Arg Ser Val Thr Glu Ile Lys Ser Glu Leu Val
 1               5                  10                  15

Leu Val Asp Asn Val Phe Thr Tyr Thr Val Lys Tyr Gly Asp Thr Leu
            20                  25                  30

Ser Thr Ile Ala Glu Ala Met Gly Ile Asp Val His Val Leu Gly Asp
        35                  40                  45

Ile Asn His Ile Ala Asn Ile Asp Leu Ile Phe Pro Asp Thr Ile Leu
    50                  55                  60

Thr Ala Asn Tyr Asn Gln His Gly Gln Ala Thr Asn Leu Thr Val Gln
65                  70                  75                  80

Ala Pro Ala Ser Ser Pro Ala Ser Val Ser His Val Pro Ser Ser Glu
```

-continued

```
                85                  90                  95

Pro Leu Pro Gln Ala Ser Ala Thr Ser Gln Pro Thr Val Pro Met Ala
            100                 105                 110

Pro Pro Ala Thr Pro Ser Asp Val Pro Thr Thr Pro Phe Ala Ser Ala
        115                 120                 125

Lys Pro Asp Ser Ser Val Thr Ala Ser Ser Glu Leu Thr Ser Ser Thr
    130                 135                 140

Asn Asp Val Ser Thr Glu Leu Ser Ser Glu Ser Gln Lys Gln Pro Glu
145                 150                 155                 160

Val Pro Gln Glu Ala Val Pro Thr Pro Lys Ala Ala Glu Thr Thr Glu
                165                 170                 175

Val Glu Pro Lys Thr Asp Ile Ser Glu Ala Pro Thr Ser Ala Asn Arg
            180                 185                 190

Pro Val Pro Asn Glu Ser Ala Ser Glu Glu Val Ser Ser Ala Ala Pro
        195                 200                 205

Ala Gln Ala Pro Ala Glu Lys Glu Glu Thr Ser Ala Pro Ala Ala Gln
    210                 215                 220

Lys Ala Val Ala Asp Thr Thr Ser Val Ala Thr Ser Asn Gly Leu Ser
225                 230                 235                 240

Tyr Ala Pro Asn His Ala Tyr Asn Pro Met Asn Ala Gly Leu Gln Pro
                245                 250                 255

Gln Thr Ala Ala Phe Lys Glu Glu Val Ala Ser Ala Phe Gly Ile Thr
            260                 265                 270

Ser Phe Ser Gly Tyr Arg Pro Gly Asp Pro Gly Asp His Gly Lys Gly
        275                 280                 285

Leu Ala Ile Asp Phe Met Val Pro Glu Asn Ser Ala Leu Gly Asp Gln
    290                 295                 300

Val Ala Gln Tyr Ala Ile Asp His Met Ala Glu Arg Gly Ile Ser Tyr
305                 310                 315                 320

Val Ile Trp Lys Gln Arg Phe Tyr Ala Pro Phe Ala Ser Ile Tyr Gly
                325                 330                 335

Pro Ala Tyr Thr Trp Asn Pro Met Pro Asp Arg Gly Ser Ile Thr Glu
            340                 345                 350

Asn His Tyr Asp His Val His Val Ser Phe Asn Ala
        355                 360
```

```
<210> SEQ ID NO 15
<211> LENGTH: 1074
<212> TYPE: DNA
<213> ORGANISM: S. pyogenes

<400> SEQUENCE: 15

caagagtgga caccacgatc ggttacagaa atcaagtctg aactcgtcct agttgataat      60

gtttttactt atacagtaaa atacggtgac actttaagca caattgctga agcaatgggg     120

attgatgtgc atgtcttagg agatattaat catattgcta atattgactt aatttttcca     180

gacacgatcc taacagcaaa ctacaatcaa cacggtcagg caacgacttt gacggttcaa     240

gcacctgctt ctagtccagc tagcgttagt catgtaccta gcagtgagcc attaccccaa     300

gcatctgcca cctctcaacc gactgttcct atggcaccat ctgcgacacc attagcatct     360

gcaaagccag atagttctgt gacagcgtca tctgagctca catcgtcaac gaatgatgtt     420

tcgactgagt cgtctagcga atcacaaaag cagccagaag taccacaaga agcagttcca     480

actcctaaag cagctgaaac gactgaagtc gaacctaaga cagacatctc agaagaccca     540
```

-continued

```
acttcagcta ataggcctgt acctaacgag agtgcttcag aagaagtttc ttctgcggcc    600

ccagcacaag ccccagcaga aaaagaagaa acctctgcgc cagcagcaca aaaagctgta    660

gctgacacca caagtgttgc aacctcaaac ggcctttctt acgctccaaa ccatgcctac    720

aatccaatga atgcagggct tcaaccacaa acagcagcct tcaaagaaga agtggcttct    780

gcctttggta ttacgtcatt tagtggttac cgtccaggtg acccaggaga tcatggtaaa    840

ggtttggcca ttgattttat ggtgcctgaa aattctgctc ttggtgatca agttgctcaa    900

tatgccattg accatatggc agagcgtggt atttcatacg ttatttggaa acagcgattc    960

tatgcgccat ttgcaagtat ttacggacca gcttacacat ggaaccccat gccagatcgc   1020

ggcagtatta cagaaaacca ttatgatcat gttcatgtct cctttaatgc ttaa         1074
```

```
<210> SEQ ID NO 16
<211> LENGTH: 357
<212> TYPE: PRT
<213> ORGANISM: S. pyogenes

<400> SEQUENCE: 16

Gln Glu Trp Thr Pro Arg Ser Val Thr Glu Ile Lys Ser Glu Leu Val
 1               5                  10                  15

Leu Val Asp Asn Val Phe Thr Tyr Thr Val Lys Tyr Gly Asp Thr Leu
            20                  25                  30

Ser Thr Ile Ala Glu Ala Met Gly Ile Asp Val His Val Leu Gly Asp
        35                  40                  45

Ile Asn His Ile Ala Asn Ile Asp Leu Ile Phe Pro Asp Thr Ile Leu
    50                  55                  60

Thr Ala Asn Tyr Asn Gln His Gly Gln Ala Thr Thr Leu Thr Val Gln
65                  70                  75                  80

Ala Pro Ala Ser Ser Pro Ala Ser Val Ser His Val Pro Ser Ser Glu
                85                  90                  95

Pro Leu Pro Gln Ala Ser Ala Thr Ser Gln Pro Thr Val Pro Met Ala
            100                 105                 110

Pro Ser Ala Thr Pro Leu Ala Ser Ala Lys Pro Asp Ser Ser Val Thr
        115                 120                 125

Ala Ser Ser Glu Leu Thr Ser Ser Thr Asn Asp Val Ser Thr Glu Ser
    130                 135                 140

Ser Ser Glu Ser Gln Lys Gln Pro Glu Val Pro Gln Glu Ala Val Pro
145                 150                 155                 160

Thr Pro Lys Ala Ala Glu Thr Thr Glu Val Glu Pro Lys Thr Asp Ile
                165                 170                 175

Ser Glu Asp Pro Thr Ser Ala Asn Arg Pro Val Pro Asn Glu Ser Ala
            180                 185                 190

Ser Glu Glu Val Ser Ser Ala Ala Pro Ala Gln Ala Pro Ala Glu Lys
        195                 200                 205

Glu Glu Thr Ser Ala Pro Ala Ala Gln Lys Ala Val Ala Asp Thr Thr
    210                 215                 220

Ser Val Ala Thr Ser Asn Gly Leu Ser Tyr Ala Pro Asn His Ala Tyr
225                 230                 235                 240

Asn Pro Met Asn Ala Gly Leu Gln Pro Gln Thr Ala Ala Phe Lys Glu
                245                 250                 255

Glu Val Ala Ser Ala Phe Gly Ile Thr Ser Phe Ser Gly Tyr Arg Pro
            260                 265                 270

Gly Asp Pro Gly Asp His Gly Lys Gly Leu Ala Ile Asp Phe Met Val
        275                 280                 285
```

-continued

```
Pro Glu Asn Ser Ala Leu Gly Asp Gln Val Ala Gln Tyr Ala Ile Asp
    290                 295                 300

His Met Ala Glu Arg Gly Ile Ser Tyr Val Ile Trp Lys Gln Arg Phe
305                 310                 315                 320

Tyr Ala Pro Phe Ala Ser Ile Tyr Gly Pro Ala Tyr Thr Trp Asn Pro
                325                 330                 335

Met Pro Asp Arg Gly Ser Ile Thr Glu Asn His Tyr Asp His Val His
            340                 345                 350

Val Ser Phe Asn Ala
        355


<210> SEQ ID NO 17
<211> LENGTH: 1113
<212> TYPE: DNA
<213> ORGANISM: S. pneumonia

<400> SEQUENCE: 17

atgaagaaaa gaatgttatt agcgtcaaca gtagccttgt catttgcccc agtattggca      60

actcaagcag aagaagttct ttggactgca cgtagtgttg agcaaatcca aaacgatttg     120

actaaaacgg acaacaaaac aagttatacc gtacagtatg gtgatacttt gagcaccatt     180

gcagaagcct tgggtgtaga tgtcacagtg cttgcgaatc tgaacaaaat cactaatatg     240

gacttgattt tcccagaaac tgttttgaca acgactgtca atgaagcaga agaagtaaca     300

gaagttgaaa tccaaacacc tcaagcagac tctagtgaag aagtgacaac tgcgacagca     360

gatttgacca ctaatcaagt gaccgttgat gatcaaactg ttcaggttgc agacctttct     420

caaccaattg cagaagttac aaagacagtg attgcttctg aagaagtggc accatctacg     480

ggcacttctg tcccagagga gcaaacgacc gaaacaactc gcccagttga agaagcaact     540

cctcaggaaa cgactccagc tgagaagcag gaaacacaag caagccctca agctgcatca     600

gcagtggaag taactacaac aagttcagaa gcaaaagaag tagcatcatc aaatggagct     660

acagcagcag tttctactta tcaaccagaa gagacgaaaa taatttcaac aacttacgag     720

gctccagctg cgcccgatta tgctggactt gcagtagcaa aatctgaaaa tgcaggtctt     780

caaccacaaa cagctgcctt taaagaagaa attgctaact tgtttggcat tacatccttt     840

agtggttatc gtccaggaga cagtggagat cacggaaaag gtttggctat cgactttatg     900

gtaccagaac gttcagaatt aggggataag attgcggaat atgctattca aaatatggcc     960

agccgtggca ttagttacat catctggaaa caacgtttct atgctccatt cgatagcaaa    1020

tatgggccag ctaacacttg gaacccaatg ccagaccgtg gtagtgtgac agaaaatcac    1080

tatgatcacg ttcacgtttc aatgaatgga taa                                 1113


<210> SEQ ID NO 18
<211> LENGTH: 370
<212> TYPE: PRT
<213> ORGANISM: S. pneumonia

<400> SEQUENCE: 18

Met Lys Lys Arg Met Leu Leu Ala Ser Thr Val Ala Leu Ser Phe Ala
1               5                   10                  15

Pro Val Leu Ala Thr Gln Ala Glu Glu Val Leu Trp Thr Ala Arg Ser
            20                  25                  30

Val Glu Gln Ile Gln Asn Asp Leu Thr Lys Thr Asp Asn Lys Thr Ser
        35                  40                  45
```

-continued

```
Tyr Thr Val Gln Tyr Gly Asp Thr Leu Ser Thr Ile Ala Glu Ala Leu
    50                  55                  60

Gly Val Asp Val Thr Val Leu Ala Asn Leu Asn Lys Ile Thr Asn Met
65                  70                  75                  80

Asp Leu Ile Phe Pro Glu Thr Val Leu Thr Thr Thr Val Asn Glu Ala
                85                  90                  95

Glu Glu Val Thr Glu Val Glu Ile Gln Thr Pro Gln Ala Asp Ser Ser
            100                 105                 110

Glu Glu Val Thr Thr Ala Thr Ala Asp Leu Thr Thr Asn Gln Val Thr
        115                 120                 125

Val Asp Asp Gln Thr Val Gln Val Ala Asp Leu Ser Gln Pro Ile Ala
    130                 135                 140

Glu Val Thr Lys Thr Val Ile Ala Ser Glu Glu Val Ala Pro Ser Thr
145                 150                 155                 160

Gly Thr Ser Val Pro Glu Glu Gln Thr Thr Glu Thr Thr Arg Pro Val
                165                 170                 175

Glu Glu Ala Thr Pro Gln Glu Thr Thr Pro Ala Glu Lys Gln Glu Thr
            180                 185                 190

Gln Ala Ser Pro Gln Ala Ala Ser Ala Val Glu Val Thr Thr Thr Ser
        195                 200                 205

Ser Glu Ala Lys Glu Val Ala Ser Ser Asn Gly Ala Thr Ala Ala Val
    210                 215                 220

Ser Thr Tyr Gln Pro Glu Glu Thr Lys Ile Ile Ser Thr Thr Tyr Glu
225                 230                 235                 240

Ala Pro Ala Ala Pro Asp Tyr Ala Gly Leu Ala Val Ala Lys Ser Glu
                245                 250                 255

Asn Ala Gly Leu Gln Pro Gln Thr Ala Ala Phe Lys Glu Glu Ile Ala
            260                 265                 270

Asn Leu Phe Gly Ile Thr Ser Phe Ser Gly Tyr Arg Pro Gly Asp Ser
        275                 280                 285

Gly Asp His Gly Lys Gly Leu Ala Ile Asp Phe Met Val Pro Glu Arg
    290                 295                 300

Ser Glu Leu Gly Asp Lys Ile Ala Glu Tyr Ala Ile Gln Asn Met Ala
305                 310                 315                 320

Ser Arg Gly Ile Ser Tyr Ile Ile Trp Lys Gln Arg Phe Tyr Ala Pro
                325                 330                 335

Phe Asp Ser Lys Tyr Gly Pro Ala Asn Thr Trp Asn Pro Met Pro Asp
            340                 345                 350

Arg Gly Ser Val Thr Glu Asn His Tyr Asp His Val His Val Ser Met
        355                 360                 365

Asn Gly
    370
```

```
<210> SEQ ID NO 19
<211> LENGTH: 1183
<212> TYPE: DNA
<213> ORGANISM: S. pyogenes
<220> FEATURE:
<221> NAME/KEY: misc_difference
<222> LOCATION: (428)...(448)
<223> OTHER INFORMATION: nnnnnnnnnnnnnnnnnnnnn can be
      ctgatgtccaacgacaccat or absent
<220> FEATURE:
<221> NAME/KEY: misc_difference
<222> LOCATION: (733)...(744)
<223> OTHER INFORMATION: nnnnnnnnnnn can be cagatgttaact or absent
<220> FEATURE:
<221> NAME/KEY: misc_difference
```

-continued

```
<222> LOCATION: (883)...(883)
<223> OTHER INFORMATION: n is g or absent
<220> FEATURE:
<221> NAME/KEY: misc_difference
<222> LOCATION: (943)...(943)
<223> OTHER INFORMATION: n is t or absent

<400> SEQUENCE: 19

atgattatta ctaaaaagag yttatttgtg acaagtgtcg ctttgtcgtt agyacctttg     60

gcgacagcrc aggcacaaga gtggacacca cgatcggtta casaaatcaa gtctgaactc    120

gtcctagttg ataatgtttt tacttatayw gtaaaatacg gtgacacttt aagcacaatt    180

gctgaagcaa tgggrattga tgtgcatgtc ttaggagata ttaatcatat tgctaatatt    240

gacytaattt ttccagacac gatcctaaca gcmaactaca aycaacacgg tcaggcaacg    300

amtttgacgg ttcaagcrcc tgcttctagt ccakctagcg ttagtcatgt acctagcagt    360

gagccattac cccaagcatc tgccacctct caaycgactr ttcctatggc accayctgcg    420

acaccatnnn nnnnnnnnnn nnnnnnnntm gcatctgcaa agccagatag ttytgtgaca    480

gcgtcatctg agctcacatc rtcaacgaat gatgtttcga ctgagtygtc tagcgaatca    540

caaaagcagc cagaagtacc acaagaagca gwwccaactc ctaaagcagc tgaamssact    600

gaagtcgaac ctaagacaga catctcagar gmyycaactt cagctaatag gcctgtacct    660

aacgrragtg cttcagaaga agyttcttct gcggccccag cacaagcycc agcagaaaaa    720

gaagaaacct ctnnnnnnnn nnnngcgcca gcagcacaaa aagctgtagc tgacaccaca    780

agtgttgcaa cctcaaaygg cctttcttac gctccaaacc atgcctacaa tccaatgaat    840

gcagggcttc aaccacaaac agcagccttc aaagaagaag tgncttctgc ctttggtatt    900

acgtcattta gtggttaccg tccaggwgay ccaggagatc atnggtaaag gwttrgccat    960

tgaytttatg gtrcckgwwa rytctrckct tggtgatcaa gttgctcaat atgccattga   1020

ccatatggca gassgtggta tttcatacgt tatttggaaa cagcgattct atgcgccatt   1080

tgcaagtatt tacggaccag cytacacatg gaaccccatg ccagatcgcg gcagtattac   1140

agwwwwccat tatgatcatg ttcatgtctc ctttaatgct taa                      1183


<210> SEQ ID NO 20
<211> LENGTH: 393
<212> TYPE: PRT
<213> ORGANISM: s. pyogenes
<220> FEATURE:
<221> NAME/KEY: VARIANT
<222> LOCATION: (18)...(18)
<223> OTHER INFORMATION: Xaa = Ala or Val
<220> FEATURE:
<221> NAME/KEY: VARIANT
<222> LOCATION: (50)...(50)
<223> OTHER INFORMATION: Xaa = Thr or Ile
<220> FEATURE:
<221> NAME/KEY: VARIANT
<222> LOCATION: (101)...(101)
<223> OTHER INFORMATION: Xaa = Thr or Asn
<220> FEATURE:
<221> NAME/KEY: VARIANT
<222> LOCATION: (112)...(112)
<223> OTHER INFORMATION: Xaa = Ala or Ser
<220> FEATURE:
<221> NAME/KEY: VARIANT
<222> LOCATION: (132)...(132)
<223> OTHER INFORMATION: Xaa = Pro or Ser
<220> FEATURE:
<221> NAME/KEY: VARIANT
<222> LOCATION: (134)...(134)
<223> OTHER INFORMATION: Xaa = Val or Ile
<220> FEATURE:
```

-continued

```
<221> NAME/KEY: VARIANT
<222> LOCATION: (139)...(139)
<223> OTHER INFORMATION: Xaa = Ser or Pro
<220> FEATURE:
<221> NAME/KEY: VARIANT
<222> LOCATION: (143)...(149)
<223> OTHER INFORMATION: Xaa Xaa Xaa Xaa Xaa Xaa Xaa = Ser Asp Val Pro
      Thr Thr pro or absent
<220> FEATURE:
<221> NAME/KEY: VARIANT
<222> LOCATION: (150)...(150)
<223> OTHER INFORMATION: Xaa = Phe or Leu
<220> FEATURE:
<221> NAME/KEY: VARIANT
<222> LOCATION: (158)...(158)
<223> OTHER INFORMATION: Xaa = Ser or Phe
<220> FEATURE:
<221> NAME/KEY: VARIANT
<222> LOCATION: (176)...(176)
<223> OTHER INFORMATION: Xaa = Leu or Ser
<220> FEATURE:
<221> NAME/KEY: VARIANT
<222> LOCATION: (191)...(191)
<223> OTHER INFORMATION: Xaa = Val or Glu
<220> FEATURE:
<221> NAME/KEY: VARIANT
<222> LOCATION: (199)...(199)
<223> OTHER INFORMATION: Xaa = Thr or Pro or Ser
<220> FEATURE:
<221> NAME/KEY: VARIANT
<222> LOCATION: (211)...(211)
<223> OTHER INFORMATION: Xaa = Asp or Ala
<220> FEATURE:
<221> NAME/KEY: VARIANT
<222> LOCATION: (212)...(212)
<223> OTHER INFORMATION: Xaa = Pro or Ser
<220> FEATURE:
<221> NAME/KEY: VARIANT
<222> LOCATION: (222)...(222)
<223> OTHER INFORMATION: Xaa = Glu or Gly
<220> FEATURE:
<221> NAME/KEY: VARIANT
<222> LOCATION: (228)...(228)
<223> OTHER INFORMATION: Xaa = Val or Ala
<220> FEATURE:
<221> NAME/KEY: VARIANT
<222> LOCATION: (242)...(245)
<223> OTHER INFORMATION: Xaa Xaa Xaa Xaa = Glu thr Ser Gln or absent
<220> FEATURE:
<221> NAME/KEY: VARIANT
<222> LOCATION: (246)...(246)
<223> OTHER INFORMATION: Xaa = Glu or Met
<220> FEATURE:
<221> NAME/KEY: VARIANT
<222> LOCATION: (247)...(247)
<223> OTHER INFORMATION: Xaa = Thr or Leu
<220> FEATURE:
<221> NAME/KEY: VARIANT
<222> LOCATION: (248)...(248)
<223> OTHER INFORMATION: Xaa = Ser or Thr
<220> FEATURE:
<221> NAME/KEY: VARIANT
<222> LOCATION: (295)...(295)
<223> OTHER INFORMATION: Xaa = Ala or Leu
<220> FEATURE:
<221> NAME/KEY: VARIANT
<222> LOCATION: (296)...(296)
<223> OTHER INFORMATION: Xaa = Ser or Leu
<220> FEATURE:
<221> NAME/KEY: VARIANT
<222> LOCATION: (297)...(297)
<223> OTHER INFORMATION: Xaa = Ala or Pro
<220> FEATURE:
<221> NAME/KEY: VARIANT
<222> LOCATION: (298)...(298)
<223> OTHER INFORMATION: Xaa = Phe or Leu
<220> FEATURE:
<221> NAME/KEY: VARIANT
<222> LOCATION: (299)...(299)
```

<223> OTHER INFORMATION: Xaa = Gly or Val
<220> FEATURE:
<221> NAME/KEY: VARIANT
<222> LOCATION: (300)...(300)
<223> OTHER INFORMATION: Xaa = Ile or Leu
<220> FEATURE:
<221> NAME/KEY: VARIANT
<222> LOCATION: (301)...(301)
<223> OTHER INFORMATION: Xaa = Thr or Arg
<220> FEATURE:
<221> NAME/KEY: VARIANT
<222> LOCATION: (302)...(302)
<223> OTHER INFORMATION: Xaa = Ser or His
<220> FEATURE:
<221> NAME/KEY: VARIANT
<222> LOCATION: (303)...(303)
<223> OTHER INFORMATION: Xaa = Phe or Leu
<220> FEATURE:
<221> NAME/KEY: VARIANT
<222> LOCATION: (304)...(304)
<223> OTHER INFORMATION: Xaa = Ser or Val
<220> FEATURE:
<221> NAME/KEY: VARIANT
<222> LOCATION: (305)...(305)
<223> OTHER INFORMATION: Xaa = Gly or Val
<220> FEATURE:
<221> NAME/KEY: VARIANT
<222> LOCATION: (306)...(306)
<223> OTHER INFORMATION: Xaa = Tyr or Thr
<220> FEATURE:
<221> NAME/KEY: VARIANT
<222> LOCATION: (307)...(307)
<223> OTHER INFORMATION: Xaa = Arg or Val
<220> FEATURE:
<221> NAME/KEY: VARIANT
<222> LOCATION: (308)...(308)
<223> OTHER INFORMATION: Xaa = Pro or Gln
<220> FEATURE:
<221> NAME/KEY: VARIANT
<222> LOCATION: (309)...(309)
<223> OTHER INFORMATION: Xaa = Gly or Glu
<220> FEATURE:
<221> NAME/KEY: VARIANT
<222> LOCATION: (310)...(310)
<223> OTHER INFORMATION: Xaa = Asp or Ile
<220> FEATURE:
<221> NAME/KEY: VARIANT
<222> LOCATION: (311)...(311)
<223> OTHER INFORMATION: Xaa = Pro or Gln
<220> FEATURE:
<221> NAME/KEY: VARIANT
<222> LOCATION: (312)...(312)
<223> OTHER INFORMATION: Xaa = Gly or Glu
<220> FEATURE:
<221> NAME/KEY: VARIANT
<222> LOCATION: (313)...(313)
<223> OTHER INFORMATION: Xaa = Asn or Ile
<220> FEATURE:
<221> NAME/KEY: VARIANT
<222> LOCATION: (314)...(314)
<223> OTHER INFORMATION: Xaa = His or Ile
<220> FEATURE:
<221> NAME/KEY: VARIANT
<222> LOCATION: (326)...(326)
<223> OTHER INFORMATION: Xaa = Glu or Val
<220> FEATURE:
<221> NAME/KEY: VARIANT
<222> LOCATION: (327)...(327)
<223> OTHER INFORMATION: Xaa = Asn or Ser
<220> FEATURE:
<221> NAME/KEY: VARIANT
<222> LOCATION: (329)...(329)
<223> OTHER INFORMATION: Xaa = Ala or Thr
<220> FEATURE:
<221> NAME/KEY: VARIANT
<222> LOCATION: (344)...(344)
<223> OTHER INFORMATION: Xaa = Glu or Asp
<220> FEATURE:
<221> NAME/KEY: VARIANT

```
<222> LOCATION: (345)...(345)
<223> OTHER INFORMATION: Xaa = Arg or Gly

<400> SEQUENCE: 20

Met Ile Ile Thr Lys Lys Ser Leu Phe Val Thr Ser Val Ala Leu Ser
 1               5                  10                  15

Leu Xaa Pro Leu Ala Thr Ala Gln Ala Gln Glu Trp Thr Pro Arg Ser
            20                  25                  30

Val Thr Glx Ile Lys Ser Glu Leu Val Leu Val Asp Asn Val Phe Thr
        35                  40                  45

Tyr Xaa Val Lys Tyr Gly Asp Thr Leu Ser Thr Ile Ala Glu Ala Met
    50                  55                  60

Gly Ile Asp Val His Val Leu Gly Asp Ile Asn His Ile Ala Asn Ile
65                  70                  75                  80

Asp Leu Ile Phe Pro Asp Thr Ile Leu Thr Ala Asn Tyr Asn Gln His
                85                  90                  95

Gly Gln Ala Thr Xaa Leu Thr Val Gln Ala Pro Ala Ser Ser Pro Xaa
            100                 105                 110

Ser Val Ser His Val Pro Ser Ser Glu Pro Leu Pro Gln Ala Ser Ala
        115                 120                 125

Thr Ser Gln Xaa Thr Xaa Pro Met Ala Pro Xaa Ala Thr Pro Xaa Xaa
    130                 135                 140

Xaa Xaa Xaa Xaa Xaa Xaa Ala Ser Ala Lys Pro Asp Ser Xaa Val Thr
145                 150                 155                 160

Ala Ser Ser Glu Leu Thr Ser Ser Thr Asn Asp Val Ser Thr Glu Xaa
                165                 170                 175

Ser Ser Glu Ser Gln Lys Gln Pro Glu Val Pro Gln Glu Ala Xaa Pro
            180                 185                 190

Thr Pro Lys Ala Ala Glu Xaa Thr Glu Val Glu Pro Lys Thr Asp Ile
        195                 200                 205

Ser Glu Xaa Xaa Thr Ser Ala Asn Arg Pro Val Pro Asn Xaa Ser Ala
    210                 215                 220

Ser Glu Glu Xaa Ser Ser Ala Ala Pro Ala Gln Ala Pro Ala Glu Lys
225                 230                 235                 240

Glu Xaa Xaa Xaa Xaa Xaa Xaa Xaa Ala Pro Ala Ala Gln Lys Ala Val
                245                 250                 255

Ala Asp Thr Thr Ser Val Ala Thr Ser Asn Gly Leu Ser Tyr Ala Pro
            260                 265                 270

Asn His Ala Tyr Asn Pro Met Asn Ala Gly Leu Gln Pro Gln Thr Ala
        275                 280                 285

Ala Phe Lys Glu Glu Val Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Gly Lys Gly Leu Ala Ile
305                 310                 315                 320

Asp Phe Met Val Pro Xaa Xaa Ser Xaa Leu Gly Asp Gln Val Ala Gln
                325                 330                 335

Tyr Ala Ile Asp His Met Ala Xaa Xaa Gly Ile Ser Tyr Val Ile Trp
            340                 345                 350

Lys Gln Arg Phe Tyr Ala Pro Phe Ala Ser Ile Tyr Gly Pro Ala Tyr
        355                 360                 365

Thr Trp Asn Pro Met Pro Asp Arg Gly Ser Ile Thr Xaa Xaa His Tyr
    370                 375                 380

Asp His Val His Val Ser Phe Asn Ala
385                 390
```

<210> SEQ ID NO 21
<211> LENGTH: 32
<212> TYPE: DNA
<213> ORGANISM: Artificial Sequence
<220> FEATURE:
<223> OTHER INFORMATION: DMAR16 Oligonucleotide

<400> SEQUENCE: 21
caggccatgg agtggacacc acgatcggtt ac 32

<210> SEQ ID NO 22
<211> LENGTH: 37
<212> TYPE: DNA
<213> ORGANISM: Artificial Sequence
<220> FEATURE:
<223> OTHER INFORMATION: DMAR17 Oligonucleotide

<400> SEQUENCE: 22
gccgctcgag agcattaaag gagacatgaa catgatc 37

<210> SEQ ID NO 23
<211> LENGTH: 25
<212> TYPE: PRT
<213> ORGANISM: Artificial Sequence
<220> FEATURE:
<223> OTHER INFORMATION: Signal peptide predicted from analysis of SEQ ID NO:2

<400> SEQUENCE: 23

Met Ile Ile Thr Lys Lys Ser Leu Phe Val Thr Ser Val Ala Leu Ser
1 5 10 15

Leu Ala Pro Leu Ala Thr Ala Gln Ala
20 25

<210> SEQ ID NO 24
<211> LENGTH: 5
<212> TYPE: PRT
<213> ORGANISM: Artificial Sequence
<220> FEATURE:
<221> NAME/KEY: VARIANT
<222> LOCATION: (3)...(3)
<223> OTHER INFORMATION: Xaa = Any Amino Acid
<220> FEATURE:
<223> OTHER INFORMATION: Cell wall anchoring motif

<400> SEQUENCE: 24

Leu Pro Xaa Thr Gly
1 5

<210> SEQ ID NO 25
<211> LENGTH: 6
<212> TYPE: PRT
<213> ORGANISM: Artificial Sequence
<220> FEATURE:
<223> OTHER INFORMATION: IgA binding motif

<400> SEQUENCE: 25

Met Leu Lys Lys Ile Glu
1 5

<210> SEQ ID NO 26
<211> LENGTH: 28
<212> TYPE: DNA
<213> ORGANISM: Artificial Sequence
<220> FEATURE:
<223> OTHER INFORMATION: DMAR69 oligonucleotide -continued

```
<400> SEQUENCE: 26

ctgggaagat tatctagcac attaatac                                    28


<210> SEQ ID NO 27
<211> LENGTH: 25
<212> TYPE: DNA
<213> ORGANISM: Artificial Sequence
<220> FEATURE:
<223> OTHER INFORMATION: DMAR72 oligonucleotide

<400> SEQUENCE: 27

cataacgtta aaactgtcta aaggg                                       25


<210> SEQ ID NO 28
<211> LENGTH: 34
<212> TYPE: DNA
<213> ORGANISM: Artificial Sequence
<220> FEATURE:
<223> OTHER INFORMATION: DMAR24 oligonucleotide

<400> SEQUENCE: 28

tacccggatc cccaagagtg gacaccacga tcgg                             34


<210> SEQ ID NO 29
<211> LENGTH: 36
<212> TYPE: DNA
<213> ORGANISM: Artificial Sequence
<220> FEATURE:
<223> OTHER INFORMATION: DMAR25 oligonucleotide

<400> SEQUENCE: 29

gcgctcgtcg acgcgtatct cagcctctta tagggc                           36
```

*STREPTOCOCCUS PYOGENES* ANTIGENS

FIELD OF THE INVENTION

The present invention is related to antigens, more particularly a polypeptide antigen of *Streptococcus pyogenes* (also called group A *Streptococcus* (GAS)) bacterial pathogen which may be useful for prophylaxis, diagnostic and/or therapy of streptococcal infection.

BACKGROUND OF THE INVENTION

*Streptococci* are gram (+) bacteria which are differentiated by group specific carbohydrate antigens A through O which are found at the cell surface. *Streptococcus pyogenes* isolates are further distinguished by type-specific M protein antigens. M proteins are important virulence factors which are highly variable both in molecular weights and in sequences. Indeed, more than 80-M protein types have been identified on the basis of antigenic differences.

*Streptococcus pyogenes* is responsible for many diverse infection types, including pharyngitis, erysipelas and impetigo, scarlet fever, and invasive diseases such as bacteremia and necrotizing fasciitis and also toxic shock. A resurgence of invasive disease in recent years has been documented in many countries, including those in North America and Europe. Although the organism is sensitive to antibiotics, the high attack rate and rapid onset of sepsis results in high morbidity and mortality.

To develop a vaccine that will protect individuals from *Streptococcus pyogenes* infection, efforts have concentrated on virulence factors such as the type-specific M proteins. However, the amino-terminal portion of M proteins was found to induce cross-reactive antibodies which reacted with human myocardium, tropomyosin, myosin, and vimentin, which might be implicated in autoimmune diseases. Others have used recombinant techniques to produce complex hybrid proteins containing amino-terminal peptides of M proteins from different serotypes. However, a safe vaccine containing all *Streptococcus pyogenes* serotypes will be highly complex to produce and standardize.

In addition to the serotype-specific antigens, other *Streptococcus pyogenes* proteins have generated interest as potential vaccine candidates. The C5a peptidase, which is expressed by at least *Streptococcus pyogenes* 40 serotypes, was shown to be immunogenic in mice, but its capacity to reduce the level of nasopharyngeal colonization was limited. Other investigators have also focused on the streptococcal pyrogenic exotoxins which appear to play an important role in pathogenesis of infection. Immunization with these proteins prevented the deadly symptoms of toxic shock, but did not prevent colonization.

Therefore there remains an unmet need for *Streptococcus pyogenes* antigens that may be used vaccine components for prophylaxis, diagnostic and/or therapy of *Streptococcus* infection.

SUMMARY OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14, 16, 20 or fragments, analogues or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14, 16, 20 or fragments, analogues or derivatives thereof.

In other aspects, there are provided novel polypeptides encoded by polynucleotides of the invention, vectors comprising polynucleotides of the invention operably linked to an expression control region, as well as host cells transfected with said vectors, pharmaceutical or vaccine compositions and methods of producing polypeptides comprising culturing said host cells under conditions suitable for expression.

BRIEF DESCRIPTION OF THE DRAWINGS

FIG. 1 is the DNA sequence of BVH-P1 gene from serotype 3 *S. pyogenes* strain ATCC12384 with a secretion signal at position 1 to 75; SEQ ID NO:1.

FIG. 2 is the amino acid sequence BVH-P1 protein from serotype 3 *S. pyogenes* strain ATCC12384 with a secretion signal at position 1 to 25; SEQ ID NO:2.

FIG. 3 is the DNA sequence of BVH-P1 gene from *S. pyogenes* strain LSPQ2699(ATCC19615) with a secretion signal at position 1 to 75; SEQ ID NO:3.

FIG. 4 is the amino acid sequence BVH-P1 protein from *S. pyogenes* strain LSPQ2699(ATCC19615) with a secretion signal at position 1 to 25; SEQ ID NO:4.

FIG. 5 is the DNA sequence of BVH-P1 gene from *S. pyogenes* strain SPY57 with a secretion signal at position 1 to 75; SEQ ID NO:5.

FIG. 6 is the amino acid sequence BVH-P1 protein from *S. pyogenes* strain SPY57 with a secretion signal at position 1 to 25; SEQ ID NO:6.

FIG. 7 is the DNA sequence of BVH-P1 gene from *S. pyogenes* strain B514 with a secretion signal at position 1 to 75; SEQ ID NO:7.

FIG. 8 is the amino acid sequence BVH-P1 protein from *S. pyogenes* strain B514 with a secretion signal at position 1 to 25; SEQ ID NO:8.

FIG. 9 is the DNA sequence BVH-P1 gene without a secretion signal from serotype 3 *S. pyogenes* strain ATCC12384; SEQ ID NO:9.

FIG. 10 is the amino acid sequence BVH-P1 protein without a secretion signal from serotype 3 *S. pyogenes* strain ATCC12384 SEQ ID NO:10.

FIG. 11 is the DNA sequence BVH-P1 gene without a secretion signal from serotype 3 *S. pyogenes* strain LSPQ2699 (ATCC19615); SEQ ID NO:11.

FIG. 12 is the amino acid sequence BVH-P1 protein without a secretion signal from serotype 3 *S. pyogenes strain LSPQ*2699 (ATCC19615); SEQ ID NO:12.

FIG. 13 is the DNA sequence BVH-P1 gene without a secretion signal from serotype 3 *S. pyogenes* strain SPY57; SEQ ID NO:13.

FIG. 14 is the amino acid sequence BVH-P1 protein without a secretion signal from serotype 3 *S. pyogenes* strain SPY57; SEQ ID NO:14.

FIG. 15 is the DNA sequence BVH-P1 gene without a secretion signal from serotype 3 *S. pyogenes* strain B514; SEQ ID NO:15.

FIG. 16 is the amino acid sequence BVH-P1 protein without a secretion signal from serotype 3 *S. pyogenes* strain B514; SEQ ID NO:16.

FIG. 17 depicts the comparison of the nucleotide sequences of the BVH-P1 genes from ATCC12384 (SEQ ID NO: 1), LSPQ2699(ATCC19615) (SEQ ID NO: 3), SPY57 (SEQ ID NO: 5), B514 (SEQ ID NO: 7), ATCC 70029 (Oklahoma) (SEQ ID NO: 32) and T28/51/4 (U09352) (SEQ ID NO: 30) *S. pyogenes* strains by using the program Clustal W from MacVector sequence analysis software (version 6.5). Underneath the alignment, there is a consensus line. Shaded nucleotides are identical between every sequences and gaps in the sequence introduced by alignment are indicated by hyphens.

FIG. 18 depicts the comparison of the predicted amino acid sequences of the BVH-P1 open reading frames from ATCC12384 (SEQ ID NO: 2), LSPQ2699(ATCC19615) (SEQ ID NO: 4), SPY57 (SEQ ID NO: 6), B514 (SEQ ID NO: 8), ATCC 70029 (Oklahoma) (SEQ ID NO: 33) and T28/51/4 (U09352) (SEQ ID NO: 31) *S. pyogenes strains* by using the program Clustal W from MacVector sequence analysis software (version 6.5). Underneath the alignment, there is a consensus line. Shaded amino acid residues are identical between every sequences and gaps in the sequence introduced by alignment are indicated by hyphens.

FIG. 19 is the DNA sequence of a gene from *S. pneumonia*; SEQ ID NO:17.

FIG. 20 is the amino acid sequence of a protein from *S. pneumonia*; SEQ ID NO:18.

DETAILED DESCRIPTION OF THE INVENTION

According to one aspect, the present invention provides an isolated polynucleotide encoding a polypeptide having at least 70% identity to a second polypeptide comprising a sequence chosen from SEQ ID NOs: 2, 4, 6, 8, 10, 12, 14, 16, 20 or fragments, analogues or derivatives thereof.

According to one aspect, the present invention provides an isolated polynucleotide encoding a polypeptide having at least 95% identity to a second polypeptide comprising a sequence chosen from SEQ ID NOs: 2, 4, 6, 8, 10, 12, 14, 16, 20 or fragments, analogues or derivatives thereof.

According to one aspect, the present invention relates to polypeptides characterized by the amino acid sequence comprising SEQ ID NOs: 2, 4, 6, 8, 10, 12, 14, 16, 20 or fragments, analogues or derivatives thereof.

According to one aspect, the present invention provides an isolated polynucleotide encoding a polypeptide capable of generating antibodies having binding specificity for a polypeptide comprising a sequence chosen from SEQ ID NOs: 2, 4, 6, 8, 10, 12, 14, 16, 20 or fragments, analogues or derivatives thereof.

In accordance with the present invention, there is provided a consensus nucleotide sequence depicted in FIG. 17. As can be seen by the alignment, the polynucleotide encoding the polypeptide of the invention is well conserved. Without restricting the scope of the invention, the following table 1 shows the possible modifications. SEQ ID NO:19 covers the consensus nucleotide sequence depicted in FIG. 17 with the modifications illustrated in Table 1:

| Position on alignment in FIG. 17 | Possible nucleotide |
|---|---|
| 21 | C or T |
| 53 | C or T |
| 69 | G or A |
| 103 | G or C |
| 149 | C or T |
| 150 | A or T |
| 195 | G or A |
| 244 | T or C |
| 273 | A or C |
| 282 | T or C |
| 302 | C or A |

-continued

| Position on alignment in FIG. 17 | Possible nucleotide |
|---|---|
| 318 | A or G |
| 334 | G or T |
| 394 | C or T |
| 400 | G or A |
| 415 | C or T |
| 428-448 | [CTGATGTCCCAACGACACCAT] (SEQ ID NO: 34) or none |
| 450 | C or A |
| 473 | C or T |
| 501 | G or A |
| 527 | T or C |
| 572 | T or A |
| 573 | T or A |
| 595 | A or C |
| 596 | C or G |
| 597 | G or C |
| 630 | A or G |
| 632 | A or C |
| 633 | C or T |
| 634 | C or T |
| 665 | A or G |
| 666 | G or A |
| 683 | T or C |
| 708 | C or T |
| 733 | [CAGATGTTAACT] (SEQ ID NO: 35) or none |
| 798 | T or C |
| 883 | G or none |
| 927 | T or A |
| 930 | T or C |
| 943 | T or none |
| 952 | T or A |
| 955 | G or A |
| 964 | T or C |
| 973 | G or A |
| 976 | T or G |
| 978 | A or T |
| 979 | A or T |
| 981 | A or G |
| 982 | T or C |
| 986 | G or A |
| 988 | T or G |
| 1033 | G or C |
| 1034 | C or G |
| 1102 | C or T |
| 1143 | A or T |
| 1144 | A or T |
| 1145 | A or T |
| 1146 | A or T |

In accordance with the present invention, there is provided a consensus amino acid sequence depicted in FIG. 18. As can be seen by the alignment, the polypeptide of the invention is well conserved. Without restricting the scope of the invention, the following table 2 shows the possible modifications. SEQ ID NO:20 covers the consensus nucleotide sequence depicted in FIG. 18 with the modifications illustrated in Table 2:

| Position on alignment in FIG. 18 | Possible amino acid |
|---|---|
| 18 | A or V |
| 35 | E or Q |
| 50 | T or I |
| 101 | T or N |
| 112 | A or S |
| 132 | P or S |

-continued

| Position on alignment in FIG. 18 | Possible amino acid |
|---|---|
| 134 | V or I |
| 139 | S or P |
| 143 to 149 | SDVPTTP (SEQ ID NO: 36) or none |
| 150 | F or L |
| 158 | S or F |
| 176 | L or s |
| 191 | V or E |
| 199 | T or P or S |
| 211 | D or A |
| 212 | P or S |
| 222 | E or G |
| 228 | V or A |
| 242 to 245 | ETSQ (SEQ ID NO: 37) or none |
| 246 | E or M |
| 247 | T or L |
| 248 | S or T |
| 295 | A or L |
| 296 | S or L |
| 297 | A or P |
| 298 | F or L |
| 299 | G or V |
| 300 | I or L |
| 301 | T or R |
| 302 | S or H |
| 303 | F or L |
| 304 | S or V |
| 305 | G or V |
| 306 | Y or T |
| 307 | R or V |
| 308 | P or Q |
| 309 | G or E |
| 310 | D or I |
| 311 | P or Q |
| 312 | G or E |
| 313 | D or I |
| 314 | H or I |
| 326 | E or V |
| 327 | N or S |
| 329 | A or T |
| 344 | E or D |
| 345 | R or G |
| 381 | E or V |
| 382 | N or F |

In accordance with the present invention, all polynucleotides encoding polypeptides are within the scope of the present invention.

In a further embodiment, the polypeptides in accordance with the present invention are antigenic.

In a further embodiment, the polypeptides in accordance with the present invention are immunogenic.

In a further embodiment, the polypeptides in accordance with the present invention can elicit an immune response in an individual.

In a further embodiment, the present invention also relates to polypeptides which are able to raise antibodies having binding specificity to the polypeptides of the present invention as defined above.

An antibody that "has binding specificity" is an antibody that recognizes and binds the selected polypeptide but which does not substantially recognize and bind other molecules in a sample, e.g., a biological sample. Specific binding can be measured using an ELISA assay in which the selected polypeptide is used as an antigen.

In accordance with the present invention, "protection" in the biological studies is defined by a significant increase in the survival curve, rate or period. Statistical analysis using the Log rank test to compare survival curves, and Fisher exact test to compare survival rates and numbers of days to death, respectively, might be useful to calculate P values and determine whether the difference between the two groups is statistically significant. P values of 0.05 are regarded as not significant.

As used herein, "fragments", "analogues" or "derivatives" of the polypeptides of the invention include those polypeptides in which one or more of the amino acid residues are substituted with a conserved or non-conserved amino acid residue (preferably conserved) and which may be natural or unnatural. In one embodiment, derivatives and analogues of polypeptides of the invention will have about 70% identity with those sequences illustrated in the figures or fragments thereof. That is, 70% of the residues are the same. In a further embodiment, polypeptides will have greater than 75% homology. In a further embodiment, polypeptides will have greater than 80% homology. In a further embodiment, polypeptides will have greater than 85% homology. In a further embodiment, polypeptides will have greater than 90% homology. In a further embodiment, polypeptides will have greater than 95% homology. In a further embodiment, polypeptides will have greater than 99% homology. In a further embodiment, derivatives and analogues of polypeptides of the invention will have less than about 20 amino acid residue substitutions, modifications or deletions and more preferably less than 10. Preferred substitutions are those known in the art as conserved i.e. the substituted residues share physical or chemical properties such as hydrophobicity, size, charge or functional groups.

The skilled person will appreciate that fragments, analogues or derivatives of the proteins or polypeptides of the invention will also find use in the context of the present invention, i.e. as antigenic/immunogenic material. Thus, for instance proteins or polypeptides which include one or more additions, deletions, substitutions or the like are encompassed by the present invention. In addition, it may be possible to replace one amino acid with another of similar "type". For instance replacing one hydrophobic amino acid with another hydropholic amino acid.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

In an alternative approach, the analogues or derivatives could be fusion proteins, incorporating moieties which render purification easier, for example by effectively tagging the desired protein or polypeptide, it may be necessary to remove the "tag" or it may be the case that the fusion protein itself retains sufficient antigenicity to be useful.

In an additional aspect of the invention there are provided antigenic/immunogenic fragments of the proteins or polypeptides of the invention, or of analogues or derivatives thereof.

The fragments of the present invention should include one or more epitopic regions or be sufficiently similar to such regions to retain their antigenic/immunogenic properties.

Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for analogues, derivatives and fragments is that they possess at least a degree of the antigenicity/immunogenic of the protein or polypeptide from which they are derived.

Also included are polypeptides which have fused thereto other compounds which alter the polypeptides biological or pharmacological properties i.e. polyethylene glycol (PEG) to increase half-life; leader or secretory amino acid sequences for ease of purification; prepro- and pro-sequences; and (poly)saccharides.

Furthermore, in those situations where amino acid regions are found to be polymorphic, it may be desirable to vary one or more particular amino acids to more effectively mimic the different epitopes of the different *streptococcus* strains.

Moreover, the polypeptides of the present invention can be modified by terminal —$NH_2$ acylation (eg. by acetylation, or thioglycolic acid amidation, terminal carbosy amidation, e.g. with ammonia or methylamine) to provide stability, increased hydrophobicity for linking or binding to a support or other molecule.

Also contemplated are hetero and homo polypeptide multimers of the polypeptide fragments, analogues and derivatives. These polymeric forms include, for example, one or more polypeptides that have been cross-linked with cross-linkers such as avidin/biotin, gluteraldehyde or dimethylsuperimidate. Such polymeric forms also include polypeptides containing two or more tandem or inverted contiguous sequences, produced from multicistronic mRNAs generated by recombinant DNA technology.

Preferably, a fragment, analog or derivative of a polypeptide of the invention will comprise at least one antigenic region i.e. at least one epitope.

In order to achieve the formation of antigenic polymers (i.e. synthetic multimers), polypeptides may be utilized having bishaloacetyl groups, nitroarylhalides, or the like, where the reagents being specific for thio groups. Therefore, the link between two mercapto groups of the different peptides may be a single bond or may be composed of a linking group of at least two, typically at least four, and not more than 16, but usually not more than about 14 carbon atoms.

In a particular embodiment, polypeptide fragments, analogues and derivatives of the invention do not contain a methionine (Met) starting residue. Preferably, polypeptides will not incorporate a leader or secretory sequence (signal sequence). The signal portion of a polypeptide of the invention may be determined according to established molecular biological techniques. In general, the polypeptide of interest may be isolated from a streptococcal culture and subsequently sequenced to determine the initial residue of the mature protein and therefore the sequence of the mature polypeptide.

According to another aspect, there are provided vaccine compositions comprising one or more streptococcal polypeptides of the invention in admixture with a pharmaceutically acceptable carrier diluent or adjuvant. Suitable adjuvants include oils i.e. Freund's complete or incomplete adjuvant; salts i.e. $AlK(SO_4)_2$, $AlNa(SO_4)_2$, $AlNH_4(SO_4)_2$, silica, kaolin, carbon polynucleotides i.e. poly IC and poly AU. Preferred adjuvants include QuilA and Alhydrogel. Vaccines of the invention may be administered parenterally by injection, rapid infusion, nasopharyngeal absorption, dermoabsorption, or bucal or oral. Pharmaceutically acceptable carriers also include tetanus toxoid.

The term vaccine is also meant to include antibodies. In accordance with the present invention, there is also provided the use of one or more antibodies having binding specificity for the polypeptides of the present invention for the treatment or prophylaxis of *streptococcus* infection and/or diseases and symptoms mediated by *streptococcus* infection.

Vaccine compositions of the invention are used for the treatment or prophylaxis of streptococcal infection and/or diseases and symptoms mediated by streptococcal infection As described in P. R. Murray (Ed, in chief),E. J. Baron, M. A. Pfaller, F. C. Tenover and R. H. Yolken. Manual of Clinical Microbiology, ASM Press, Washington, D.C. sixth edition, 1995, 1482p which are herein incorporated by reference. In one embodiment, vaccine compositions of the present invention are used for the prophylaxis or treatment of pharyngitis, erysipelas and impetigo, scarlet fever, and invasive diseases such as bacteremia and necrotizing fasciitis and also toxic shock. In one embodiment, vaccine compositions of the invention are used for the prophylaxis or treatment of *streptococcus* infection and/or diseases and symptoms mediated by *streptococcus* infection, in particular group A *streptococcus* (*pyogenes*), group B *streptococcus* (GBS or agalactiae), *S. pneumoniae, dysgalactiae, uberis, nocardia* as well as *Staphylococcus aureus*. In a further embodiment, the *streptococcus* infection is *Streptococcus pyogenes*.

In a particular embodiment, vaccines are administered to those individuals at risk of *streptococcus* infection such as infants, elderly and immunocompromised individuals.

As used in the present application, the term "individuals" include mammals. In a further embodiment, the mammal is human.

Vaccine compositions are preferably in unit dosage form of about 0.001 to 100 μg/kg (antigen/body weight) and more preferably 0.01 to 10 μg/kg and most preferably 0.1 to 1 μg/kg 1 to 3 times with an interval of about 1 to 6 week intervals between immunizations.

Vaccine compositions are preferably in unit dosage form of about 0.1 μg to 10 mg and more preferably 1 μg to 1 mg and most preferably 10 to 100 μg 1 to 3 times with an interval of about 1 to 6 week intervals between immunizations.

According to another aspect, there are provided polynucleotides encoding polypeptides characterized by the amino acid sequence chosen from SEQ ID NOs: 2, 4, 6, 8, 10, 12, 14, 16, 20 or fragments, analogues or derivatives thereof.

In one embodiment, polynucleotides are those illustrated in SEQ ID NOs: 1, 3, 5, 7, 9, 11, 13, 15, 19 which may include the open reading frames (ORF), encoding polypeptides of the invention.

It will be appreciated that the polynucleotide sequences illustrated in the figures may be altered with degenerate codons yet still encode the polypeptides of the invention. Accordingly the present invention further provides polynucleotides which hybridize to the polynucleotide sequences herein above described (or the complement sequences thereof) having 50% identity between sequences. In one embodiment, at least 70% identity between sequences. In one embodiment, at least 75% identity between sequences. In one embodiment, at least 80% identity between sequences. In one embodiment, at least 85% identity between sequences. In one embodiment, at least 90% identity between sequences. In a further embodiment, polynucleotides are hybridizable under stringent conditions i.e. having at least 95% identity. In a further embodiment, more than 97% identity.

Suitable stringent conditions for hybridation can be readily determined by one of skilled in the art (see for example Sambrook et al., (1989) Molecular cloning: A Laboratory Manual, 2$^{nd}$ ed, Cold Spring Harbor, N.Y.; Current Protocols in Molecular Biology, (1999) Edited by Ausubel F. M. et al., John Wiley & Sons, Inc., N.Y.).

In a further embodiment, the present invention provides polynucleotides that hybridise under stringent conditions to either (a) a DNA sequence encoding a polypeptide or (b) the complement of a DNA sequence encoding a polypeptide;

wherein said polypeptide comprising a sequence chosen from SEQ ID NOs: 2, 4, 6, 8, 10, 12, 14, 16, 20 or fragments or analogues thereof.

In a further embodiment, the present invention provides polynucleotides that hybridise under stringent conditions to either (a) a DNA sequence encoding a polypeptide or (b) the complement of a DNA sequence encoding a polypeptide;

wherein said polypeptide comprises at least 10 contiguous amino acid residues from a polypeptide comprising a sequence chosen from SEQ ID NOs: 2, 4, 6, 8, 10, 12, 14, 16, 20 or fragments or analogues thereof.

In a further embodiment, polynucleotides are those encoding polypeptides of the invention illustrated in SEQ ID NOs: 2, 4, 6, 8, 10, 12, 14, 16, 20.

In a further embodiment, polynucleotides are those illustrated in SEQ ID NOs: 1, 3, 5, 7, 9, 11, 13, 15, 19 encoding polypeptides of the invention.

As will be readily appreciated by one skilled in the art, polynucleotides include both DNA and RNA.

The present invention also includes polynucleotides complementary to the polynucleotides described in the present application.

In a further aspect, polynucleotides encoding polypeptides of the invention, or fragments, analogues or derivatives thereof, may be used in a DNA immunization method. That is, they can be incorporated into a vector which is replicable and expressible upon injection thereby producing the antigenic polypeptide in vivo. For example polynucleotides may be incorporated into a plasmid vector under the control of the CMV promoter which is functional in eukaryotic cells. Preferably the vector is injected intramuscularly.

According to another aspect, there is provided a process for producing polypeptides of the invention by recombinant techniques by expressing a polynucleotide encoding said polypeptide in a host cell and recovering the expressed polypeptide product. Alternatively, the polypeptides can be produced according to established synthetic chemical techniques i.e. solution phase or solid phase synthesis of oligopeptides which are ligated to produce the full polypeptide (block ligation).

General methods for obtention and evaluation of polynucleotides and polypeptides are described in the following references: Sambrook et al, Molecular Cloning: A Laboratory Manual, 2nd ed, Cold Spring Harbor, N.Y., 1989; Current Protocols in Molecular Biology, Edited by Ausubel F. M. et al., John Wiley and Sons, Inc. New York; PCR Cloning Protocols, from Molecular Cloning to Genetic Engineering, Edited by White B. A., Humana Press, Totowa, N.J., 1997, 490 pages; Protein Purification, Principles and Practices, Scopes R. K., Springer-Verlag, New York, 3rd Edition, 1993, 380 pages; Current Protocols in Immunology, Edited by Coligan J. E. et al., John Wiley & Sons Inc., New York which are herein incorporated by reference.

For recombinant production, host cells are transfected with vectors which encode the polypeptide, and then cultured in a nutrient media modified as appropriate for activating promoters, selecting transformants or amplifying the genes. Suitable vectors are those that are viable and replicable in the chosen host and include chromosomal, non-chromosomal and synthetic DNA sequences e.g. bacterial plasmids, phage DNA, baculovirus, yeast plasmids, vectors derived from combinations of plasmids and phage DNA. The polypeptide sequence may be incorporated in the vector at the appropriate site using restriction enzymes such that it is operably linked to an expression control region comprising a promoter, ribosome binding site (consensus region or Shine-Dalgarno sequence), and optionally an operator (control element). One can select individual components of the expression control region that are appropriate for a given host and vector according to established molecular biology principles (Sambrook et al, Molecular Cloning: A Laboratory Manual, 2nd ed, Cold Spring Harbor, N.Y., 1989; Current Protocols in Molecular Biology, Edited by Ausubel F. M. et al., John. Wiley and Sons, Inc. New York incorporated herein by reference). Suitable promoters include but are not limited to LTR or SV40 promoter, *E. coli* lac, tac or trp promoters and the phage lambda $P_L$ promoter. Vectors will preferably incorporate an origin of replication as well as selection markers i.e. ampicilin resistance gene. Suitable bacterial vectors include pET, pQE70, pQE60, pQE-9, pbs, pD10 phagescript, psiX174, pbluescript SK, pbsks, pNH8A, pNH16a, pNH18A, pNH46A, ptrc99a, pKK223-3, pKK233-3, pDR540, pRIT5 and eukaryotic vectors pBlueBacIII, pWLNEO, pSV2CAT, pOG44, pXT1, pSG, pSVK3, pBPV, pMSG and pSVL. Host cells may be bacterial i.e. *E. coli, Bacillus subtilis, Streptomyces*; fungal i.e. *Aspergillus niger, Aspergillus nidulins*; yeast i.e. *Saccharomyces* or eukaryotic i.e. CHO, COS.

Upon expression of the polypeptide in culture, cells are typically harvested by centrifugation then disrupted by physical or chemical means (if the expressed polypeptide is not secreted into the media) and the resulting crude extract retained to isolate the polypeptide of interest. Purification of the polypeptide from culture media or lysate may be achieved by established techniques depending on the properties of the polypeptide i.e. using ammonium sulfate or ethanol precipitation, acid extraction, anion or cation exchange chromatography, phosphocellulose chromatography, hydrophobic interaction chromatography, hydroxylapatite chromatography and lectin chromatography. Final purification may be achieved using HPLC.

The polypeptide may be expressed with or without a leader or secretion sequence. In the former case the leader may be removed using post-translational processing (see U.S. Pat. No. 4,431,739; U.S. Pat. No. 4,425,437; and U.S. Pat. No. 4,338,397 incorporated herein by reference) or be chemically removed subsequent to purifying the expressed polypeptide.

According to a further aspect, the streptococcal polypeptides of the invention may be used in a diagnostic test for *streptococcus* infection, in particular *Streptococcus pyogenes* infection. Several diagnostic methods are possible, for example detecting *streptococcus* organism in a biological sample, the following procedure may be followed:

a) obtaining a biological sample from an individual;

b) incubating an antibody or fragment thereof reactive with a *streptococcus* polypeptide of the invention with the biological sample to form a mixture; and c) detecting specifically bound antibody or bound fragment in the mixture which indicates the presence of *streptococcus*.

Alternatively, a method for the detection of antibody specific to a *streptococcus* antigen in a biological sample containing or suspected of containing said antibody may be performed as follows:

a) obtaining a biological sample from an individual;

b) incubating one or more *streptococcus* polypeptides of the invention or fragments thereof with the biological sample to form a mixture; and c) detecting specifically bound antigen or bound fragment in the mixture which indicates the presence of antibody specific to *streptococcus*.

One of skill in the art will recognize that this diagnostic test may take several forms, including an immunological test such as an enzyme-linked immunosorbent assay (ELISA), a radioimmunoassay or a latex agglutination assay, essentially to determine whether antibodies specific for the protein are present in an individual.

The DNA sequences encoding polypeptides of the invention may also be used to design DNA probes for use in detecting the presence of *streptococcus* in a biological sample suspected of containing such bacteria. The detection method of this invention comprises:

a) obtaining the biological sample from an individual;

b) incubating one or more DNA probes having a DNA sequence encoding a polypeptide of the invention or fragments thereof with the biological sample to form a mixture; and c) detecting specifically bound DNA probe in the mixture which indicates the presence of *streptococcus* bacteria.

The DNA probes of this invention may also be used for detecting circulating *streptococcus* i.e. *Streptococcus pyogenes* nucleic acids in a sample, for example using a polymerase chain reaction, as a method of diagnosing *streptococcus* infections. The probe may be synthesized using conventional techniques and may be immobilized on a solid phase, or may be labelled with a detectable label. A preferred DNA probe for this application is an oligomer having a sequence complementary to at least about 6 contiguous nucleotides of the *Streptococcus pyogenes* polypeptides of the invention.

Another diagnostic method for the detection of *streptococcus* in an individual comprises:

a) labelling an antibody reactive with a polypeptide of the invention or fragment thereof with a detectable label;

b) administering the labelled antibody or labelled fragment to the patient; and c) detecting specifically bound labelled antibody or labelled fragment in the patient which indicates the presence of *streptococcus*.

A further aspect of the invention is the use of the *streptococcus* polypeptides of the invention as immunogens for the production of specific antibodies for the diagnosis and in particular the treatment of *streptococcus* infection. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *Streptococcus pyogenes* polypeptides but is preferably specific for one.

A further aspect of the invention is the use of the antibodies directed to the *streptococcus* polypeptides of the invention for passive immunization. One could use the antibodies described in the present application. Suitable antibodies may be determined using appropriate screening methods, for example by measuring the ability of a particular antibody to passively protect against *streptococcus* infection in a test model. One example of an animal model is the mouse model described in the examples herein. The antibody may be a whole antibody or an antigen-binding fragment thereof and may belong to any immunoglobulin class. The antibody or fragment may be of animal origin, specifically of mammalian origin and more specifically of murine, rat or human origin. It may be a natural antibody or a fragment thereof, or if desired, a recombinant antibody or antibody fragment. The term recombinant antibody or antibody fragment means antibody or antibody fragment which was produced using molecular biology techniques. The antibody or antibody fragments may be polyclonal, or preferably monoclonal. It may be specific for a number of epitopes associated with the *streptococcus pneumoniae* polypeptides but is preferably specific for one.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE 1

This example illustrates the cloning of *S. pyogenes* gene.

The coding region of *S. pyogenes* gene BVH-P1 (SEQ ID NO:1) was amplified by PCR (DNA Thermal Cycler Genenp PCR system 2400 Perkin Elmer, San Jose, Calif.) from genomic DNA of serotype 3 *S. pyogenes* strain ATCC12384 using the following oligos that contained base extensions for the addition of restriction sites NcoI (CCATGG) and XhoI (CTCGAG): DMAR16 (5'-CAGGCCATGGAGTGGA-CACCACGATCGGTTAC-3') (SEQ ID NO: 21); DMAR17 (5'-GCCGCTCGAGAGCATTAAAGGAGACAT-GAACATGATC-3') (SEQ ID NO: 22). PCR products were purified from agarose gel using a QIAquick gel extraction kit from QIAgen following the manufacturer's instructions (Chatsworth, Calif.), and digested with NcoI and XhoI (Pharmacia Canada Inc, Baie d'Urfé, Canada). The pET-21d (+) vector (Novagen, Madison, Wis.) was digested with NcoI and XhoI and purified from agarose gel using a QIAquick gel extraction kit from QIAgen (Chatsworth, Calif.). The NcoI-XhoI PCR products were ligated to the NcoI-XhoI pET-21d(+)expression vector. The ligated products were transformed into *E. coli* strain *E. coli* strain DH5α [φ80dlacZΔM15 Δ(lacZYA-argF)U169 endA1 recA1 hsdR17($r_K$–$m_K$+) deoR thi-1 supE44 $\lambda^-$gyrA96 relA1] (Gibco BRL, Gaithersburg, Md.) according to the method of Simanis (Hanahan, D. DNA Cloning, 1985, D. M. Glover (ed), pp. 109-135). Recombinant pET-21d(+)plasmid (rpET21d(+)) containing BVH-P1 gene was purified using a QIAgen plasmid kit (Chatsworth, Calif.) and DNA insert was sequenced (Taq Dye Deoxy Terminator Cycle Sequencing kit, ABI, Foster City, Calif.).

It was determined that the open reading frame (ORF) which codes for BVHP1 contains 1170-bp and encodes a 389 amino acid residues polypeptide with a predicted pI of 4.37 and a predicted molecular mass of 41054 Da.

Analysis of the predicted amino acid residues sequence (SEQ ID NO:2)using the Spscan sofware (Wisconsin Sequence Analysis Package; Genetics Computer Group) suggested the existence of a 25 amino acid residues signal peptide (MIITKKSLFVTSVALSLAPLATAQA) (SEQ ID NO: 23), which ends with a cleavage site situated between an alanine and a glutamine residues. Analysis of this ORF did not revealed the presence of repetitive structures, cell wall anchoring motif (LPXTG) (SEQ ID NO: 24), or IgA binding motif (MLKKIE) (SEQ ID NO: 25).

An ORF which shares 62% with the *S. pyogenes* BVH-P1 gene was initially presented in the patent application PCT/CA99/00114 which described Group B *streptococcus* antigens. BVH-P1 gene was also found to share homology (62% identity) with an ORF present in the genome of *S. pneumoniae* (The Institute for Genomic Research).

EXAMPLE 2

This example describes the PCR amplification and sequencing of BVH-P1 gene from other *S. pyogenes* strains and the evaluation of the level of molecular conservation of this gene.

Lancefield's serogroup A *S. pyogenes* LSPQ2296 (ATCC 19615) was provided by the laboratoire de la santé publique du Québec, Sainte-Anne-de-Bellevue; serotype 1 *S. pyogenes* SPY57 clinical isolate was provided by the centre de recherche en infectiologie du centre hospitalier de l'universit éLaval, Sainte-Foy; and *S. pyogenes* strain B514 which was initially isolated from a mouse was provided by Susan Hollingshead, from University of Alabama, Birmingham. The respective coding region of *S. pyogenes* gene BVH-P1 from strains ATCC 12384 (SEQ ID NO:1), LSPQ2699 (ATCC19615) (SEQ ID NO:3), SPY57 (SEQ ID NO:5), and B514 (SEQ ID NO:7) were amplified by PCR (DNA Thermal Cycler GeneAmp PCR system 2400 Perkin Elmer, San Jose, Calif.) from bacterial cell lysates using the following oligos DMAR69 (5'-CTGGGAAGATTATCTAGCACATTAATAC-3') (SEQ ID NO: 26); DMAR72 (5'-CATAACGTTAAAACTGTCTAAAGGG-3') (SEQ ID NO: 27). PCR products were purified from agarose gel using a QIAquick gel extraction kit from QIAgen following the manufacturer's instructions (Chatsworth, Calif.) and the DNA insert were sequenced (Taq Dye Deoxy Terminator Cycle Sequencing kit, ABI, Foster City, Calif.). The predicted amino acid sequences from strains ATCC12384 (SEQ ID NO:2), LSPQ2699(ATCC19615) (SEQ ID NO:4), SPY57 (SEQ ID NO:6), and B514 (SEQ ID NO:8) were respectively presented in the following FIGS. 2, 4, 6, and 8.

The FIGS. 17 and 18 respectively depict the consensus nucleotide and predicted amino acid sequences established for *S. pyogenes* BVH-P1. In addition to the sequences presented herewith, the BVH-P1 gene sequences from the genome sequencing project at the University of Oklahoma (serotype M1 *S. pyogenes* strain ATCC 70029: http://dnal.chem.ou.edu/strep.html) and from (Kil et al. 1994. Infect. Immun. 62:2440-2449: GenBank accession number U09352) were also included. No function or role in the pathogenesis of the bacteria or protection against infection was described by Kil et al. for the sequence with GenBank accession number U09352. This latter sequence presented by Kil et al. was shown to be located upstream of a *S. pyogenes* 67 kDa myosin-cross-reactive antigen.

Pairwise comparison of the BVH-P1 predicted protein sequences revealed between 95 to 100% identity with the exception of the BVH-P1 sequence obtained from GenBank under the accesssion number U09352. Pairwise comparison of that particular sequence with the other five BVH-P1 sequences indicated identity between 87 to 91%. This lower homology can be explained by the presence of two regions (119-124 and 262-281) which are more divergent comparatively to the other BVH-P1 gene sequences. Beside these two regions in the BVH-P1 sequence obtained from GenBank under the accesssion number U09352, the BVH-P1 genes showed great similarity in overall organization.

EXAMPLE 3

This example illustrates the cloning of *S. pyogenes* protein gene in CMV plasmid pCMV-GH.

The DNA coding region of a *S. pyogenes* protein was inserted in phase downstream of a human growth hormone (hGH) gene which was under the transcriptional control of the cytomegalovirus (CMV) promotor in the plasmid vector pCMV-GH (Tang et al., Nature, 1992, 356:152). The CMV promotor is a non functional plasmid in *E. coli* cells but is active upon administration of the plasmid in eukaryotic cells. The vector also incorporated the ampicillin resistance gene.

The coding region of BVH-P1 gene (SEQ ID NO:9) without its leader peptide region was amplified by PCR (DNA Thermal Cycler GeneAmp PCR system 2400 Perkin Elmer, San Jose, Calif.) from genomic DNA of serotype 3 *S. pyogenes* strain ATCC12384 using the following oligos that contained base extensions for the addition of restriction sites BamHI (GGATCC) and SalI (GTCGAC): DMAR24 (5'-TACCCGGATCCCCAAGAGTGGACACCACGATCGG-3') (SEQ ID NO: 28); DMAR25 (5'-GCGCTCGTCGACGCGTATCTCAGCCTCTTATAGGGC-3') (SEQ ID NO: 29). The PCR product was purified from agarose gel using a QIAquick gel extraction kit from QIAgen (Chatsworth, Calif.), digested with restriction enzymes (Pharmacia Canada Inc, Baie d'Urfe, Canada). The pCMV-GH vector (Laboratory of Dr. Stephen A. Johnston, Department of Biochemistry, The University of Texas, Dallas, Tex.) was digested with BamHI and SalI and purified from agarose gel using the QIAquick gel extraction kit from QIAgen (Chatsworth, Calif.). The BamHI-SalI DNA fragments were ligated to the BamHI-SalI pCMV-GH vector to create the hGH-BVH-P1 fusion protein under the control of the CMV promoter. The ligated products were transformed into *E. coli* strain DH5$\alpha$ [$\phi$80dlacZ$\Delta$M15 $\Delta$(lacZYA-argF)U169 endA1 recA1 hsdR17($r_K$–$m_K$+) deoR thi-1 supE44 $\lambda^-$gyrA96 relA1] (Gibco BRL, Gaithersburg, Md.) according to the method of Simanis (Hanahan, D. DNA Cloning, 1985, D. M. Glover (ed), pp. 109-135). The recombinant pCMV plasmid was purified using a QIAgen plasmid kit (Chatsworth, Calif.) and the nucleotide sequence of the DNA insert was verified by DNA sequencing.

EXAMPLE 4

This example illustrates the use of DNA to elicit an immune response to *S. pyogenes* antigens.

A group of 8 female BALB/c mice (Charles River, St-Constant, Québec, Canada) were immunized by intramuscular injection of 100 μl three times at two- or three-week intervals with 50 μg of recombinant PCMV-GH encoding BVH-P1 gene in presence of 50 μg of granulocyte-macrophage colony-stimulating factor (GM-CSF)-expressing plasmid pCMV-GH-GM-CSF (Laboratory of Dr. Stephen A. Johnston, Department of Biochemistry, The University of Texas, Dallas, Tex.). As control, a group of mice were injected with 50 μg of pCMV-GH in presence of 50 μg of pCMV-GH-GM-CSF. Blood samples were collected from the orbital sinus prior to each immunization and seven days following the third injection and serum antibody responses were determined by ELISA using purified BVH-P1-His•Tag from SEQ ID NO:11 *S. pyogenes* recombinant protein as coating antigen.

EXAMPLE 5

This example illustrates the production and purification of recombinant *S. pyogenes* BVH-P1 protein.

The recombinant pET-21d(+)plasmid with BVH-P1 gene corresponding to the SEQ ID NO:9 was used to transform by electroporation (Gene Pulser II apparatus, BIO-RAD Labs, Mississauga, Canada) *E. coli* strain BL21(DE3) ($F^{-}$ompT hsd$S_B$ ($r^{-}_{B}m^{-}_{B}$) gal dcm (DE3)) (Novagen, Madison, Wis.). In this strain of *E. coli*, the T7 promotor controlling expression of the recombinant protein is specifically recognized by the T7 RNA polymerase (present on the λDE3 prophage) whose gene is under the control of the lac promotor which is inducible by isopropyl-β-d-thio-galactopyranoside (IPTG). The transformant BL21(DE3)/rpET was grown at 37° C. with agitation at 250 rpm in LB broth (peptone 10 g/L, yeast extract 5 g/L, NaCl 10 g/L) containing 100 μg of carbenicillin (Sigma-Aldrich Canada Ltd., Oakville, Canada) per ml until the $A_{600}$ reached a value of 0.6. In order to induce the production of *S. pyogenes* BVH-P1-His•Tag recombinant protein (from SEQ ID NO:10), the cells were incubated for 3 additional hours in the presence of IPTG at a final concentration of 1 mM. Induced cells from a 500 ml culture were pelleted by centrifugation and frozen at −70° C.

The purification of the recombinant proteins from the soluble cytoplasmic fraction of IPTG-induced BL21(DE3)/rpET21b(+) was done by affinity chromatography based on the properties of the His•Tag sequence (6 consecutive histidine residues) to bind to divalent cations ($Ni^{2+}$) immobilized on the His•Bind metal chelation resin. Briefly, the pelleted cells obtained from a 500 mL culture induced with IPTG was resuspended in lysis buffer (20 mM Tris, 500 mM NaCl. 10 mM imidazole, pH 7.9) containing 1 mM PMSF, sonicated and centrifuged at 12,000×g for 20 min to remove debris. The supernatant was deposited on a Ni-NTA agarose column (Qiagen, Mississauga, Ontario, Canada). The *S. pyogenes* BVH-P1-His•Tag recombinant protein (from SEQ ID NO:10) was eluted with 250 mM imidazole-500 mM NaCl-20 mM Tris pH 7.9. The removal of the salt and imidazole from the sample was done by dialysis against PBS at 4° C. The quantities of recombinant protein obtained from the soluble fraction of *E. coli* was estimated by MicroBCA (Pierce, Rockford, Ill.).

EXAMPLE 6

This example illustrates the accessibility to antibodies of the BVH-P1 protein at the surface of *S. pyogenes* strain.

Bacteria were grown in Tood Hewitt (TH) broth (Difco Laboratories, Detroit Mich.) with 0.5% Yeast extract (Difco Laboratories) and 0.5% peptone extract (Merck, Darmstadt, Germany) at 37° C. in a 8% $CO_2$ atmosphere to give an $OD_{490nm}$ of 0.600 (~$10^8$ CFU/ml). Dilutions of anti-BVH-P1 or control sera were then added and allowed to bind to the cells, which were incubated for 2 h at 4° C. Samples were washed 4 times in blocking buffer [phosphate-buffered saline (PBS) containing 2% bovine serum albumin (BSA)], and then 1 ml of goat fluorescein (FITC)-conjugated anti-mouse IgG+IgM diluted in blocking buffer was added. After an additional incubation of 60 min at room temperature, samples were washed 4 times in blocking buffer and fixed with 0.25% formaldehyde in PBS buffer for 18-24 h at 4° C. Cells were washed 2 times in PBS buffer and resuspended in 500 μl of PBS buffer. Cells were kept in the dark at 4° C. until analyzed by flow cytometry (Epics® XL; Beckman Coulter, Inc.). Flow cytometric analysis revealed that BVH-P1-specific antibodies efficiently recognized their corresponding surface exposed epitopes on both the homologous (ATCC12384; serotype3) and the heterologous (SPY57; seotype 1) *S. pyogenes* strains tested. It was determined that more than 90% of the 10,000 *S. pyogenes* cells analyzed were labeled with the antobodies present in the BVH-MC1 specific anti-sera. These observations clearly demonstrate that the BVH-P1 protein is accessible at the surface where it can be easily recognized by antibodies. Anti-*S. pyogenes* antibodies were shown to play an important role in the protection against *S. pyogenes* infection.

EXAMPLE 7

This example illustrates the protection against fatal *S. pyogenes* infection induced by passive immunization of mice with rabbit hyper-immune sera.

New Zealand rabbits (Charles River laboratories, Montreal, Canada) were injected subcutaneously at multiple sites with approximately 50 μg and 100 μg of BVH-P1-His•Tag protein (from SEQ ID NO:10) that was produced and purified as described in Example 5 and adsorbed to Alhydrogel adjuvant (Superfos Biosector a/s). Rabbits were immunized three times at three-week intervals with the BVH-P1-His•Tag protein (from SEQ ID NO:10). Blood samples were collected three weeks after the third injection. The antibodies present in the serum were purified by precipitation using 40% saturated ammonium sulfate. Groups of 10 female CD-1 mice (Charles River) were injected intravenously with 500 μl of purified serum collected either from BVH-P1-His•Tag (from SEQ ID NO:10) immunized rabbits or rabbits immunized with an unrelated control recombinant protein. Eighteen hours later the mice were challenged with approximately $2\times10^7$ CFU of the type 3 *S. pyogenes* strain ATCC12384. Samples of the *S. pyogenes* challenge inoculum were plated on blood agar plates to determine the CFU and to verify the challenge dose. Deaths were recorded for a period of 5 days.

EXAMPLE 8

This example illustrates the protection of mice against fatal *S. pyogenes* infection induced by immunization with BVH-P1 protein.

Groups of 8 female CD-1 mice (Charles River) were immunized subcutaneously three times at three-week intervals with 20 μg of affinity purified *S. pyogenes* BVH-P1-His•Tag recombinant protein (from SEQ ID NO:10) in presence of 10 μg of QuilA adjuvant (Cedarlane Laboratories Ltd, Hornby, Canada) or, as control, with QuilA adjuvant alone in PBS. Blood samples were collected from the orbital sinus on day 1, 22 and 43 prior to each immunization and seven days (day 50) following the third injection. Analysis by ELISA using purified recombinant BVH-P1 protein (from SEQ ID NO:10) clearly indicated that this protein is highly immunogenic in animals. Indeed reciprocal ELISA titers higher than $10^6$ were determined for the mice immunized with this recombinant protein. Two weeks later the mice were challenged with approximately $2\times10^7$ CFU of the type 3 *S. pyogenes* strain ATCC12384. Samples of the *S. pyogenes* challenge inoculum were plated on blood agar plates to determine the CFU and to verify the challenge dose. Deaths were recorded for a period of 5 days. Five out of the 8 (62%) mice immunized with three injections of 20 μg of purified recombinant BVH-P1 (from SEQ ID NO:10) and QuilA adjuvant survived the bacterial challenge to only 2/7 (28%)in the control group.

TABLE 3

Immunization of CD-1 mice with purified recombinant BVH-P1 protein confers protection against subsequent challenge with *S. pyogenes* strain ATCC 12384

| | Survival of the mice challenged with *S. pyogenes* strain ATCC 12384 (Day after challenge: number of survivors/total number of mice challenged)) | | | | |
|---|---|---|---|---|---|
| Groups | 1 | 2 | 3 | 4 | 5 |
| 20 μg of BVH-P1-His•Tag | 8/8 | 8/8 | 7/8 | 6/8 | 5/8 |
| Control | 7/7 | 6/7 | 3/7 | 2/7 | 2/7 |

What is claimed is:

1. An isolated polypeptide comprising the amino acid sequence set forth in SEQ ID NO: 2, 4, 6, 8, 10, 12, 14, 16, or 33.

2. An isolated polypeptide according to claim 1, wherein the N-terminal Met residue of SEQ ID NO: 2, 4, 6, 8, or 33 is deleted.

3. A composition comprising the polypeptide according to claim 1 and a pharmaceutically acceptable carrier, diluent or adjuvant.

4. A composition comprising the polypeptide according to claim 2 and a pharmaceutically acceptable carrier, diluent or adjuvant.

5. A method for therapeutic treatment of a *Streptococcus pyogenes* infection in an individual, comprising administering to said individual a therapeutic amount of the polypeptide of claim 1.

6. A method for therapeutic treatment of a *Streptococcus pyogenes* infection in an individual, comprising administering to said individual a therapeutic amount of the polypeptide of claim 2.

7. An isolated BVH-P1 polypeptide which is encoded by a polynucleotide that is capable of being amplified by polymerase chain reaction from DNA using oligonucleotides of SEQ ID NO: 26 and SEQ ID NO: 27, wherein said polypeptide has at least 95% sequence identity along its entire length to the amino acid sequence set forth in SEQ ID NO: 2, 4, 6, 8, 10, 12, 14, 16, 20 or 33, and which is capable of eliciting antibodies specific to *Streptococcus pyogenes,* wherein said polypeptide does not have the amino acid sequence set forth in SEQ ID NO: 31.

8. The isolated BVH-P1 polypeptide of claim 7, wherein said DNA is *Streptococcus pyogenes* genomic DNA.

9. The Anisolated polypeptide of claim 7, wherein said polypeptide has more than 97% sequence identity.

10. An isolated polypeptide comprising the amino acid sequence set forth in SEQ ID NO: 20 wherein the polypeptide does not comprise the amino acid sequence set forth in SEQ ID NO: 31.

11. The polypeptide according to claim 10, wherein the N-terminal Met residue of SEQ ID NO: 20 is deleted.

* * * * *

UNITED STATES PATENT AND TRADEMARK OFFICE

CERTIFICATE OF CORRECTION

PATENT NO. : 7,247,308 B2
APPLICATION NO. : 10/332231
DATED : July 24, 2007
INVENTOR(S) : Denis Martin et al.

It is certified that error appears in the above-identified patent and that said Letters Patent is hereby corrected as shown below:

Column 58

Line 50, "Anisolated" should read as -- isolated --

Signed and Sealed this

Sixth Day of May, 2008

JON W. DUDAS
*Director of the United States Patent and Trademark Office*